United States Patent [19]
Bhattacharjee et al.

[11] Patent Number: 5,919,617
[45] Date of Patent: Jul. 6, 1999

[54] METHODS AND REAGENTS FOR DETECTING FUNGAL PATHOGENS IN A BIOLOGICAL SAMPLE

[75] Inventors: Jnanendra K. Bhattacharjee, Oxford, Ohio; Richard C. Garrad, Columbia, Mo.; Paul L. Skatrud, Greenwood; Robert B. Peery, Brownsburg, both of Ind.

[73] Assignee: Miami University, Oxford, Ohio

[21] Appl. No.: 08/360,606

[22] Filed: Dec. 21, 1994

[51] Int. Cl.$^6$ ............... C12Q 1/68; C07H 21/02; C07H 21/04; C12P 19/34
[52] U.S. Cl. ............ 435/6; 536/23.1; 536/24.32; 435/91.1; 435/91.2
[58] Field of Search ............... 435/6, 91.2, 174, 435/285.1, 287.1, 287.2, 91.1; 536/23.1, 24.3, 24.32, 26.6; 422/99

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,889,818 | 12/1989 | Gelfand et al. | 435/194 |
| 4,965,188 | 10/1990 | Mullis et al. | 435/6 |
| 5,075,216 | 12/1991 | Innis et al. | 435/6 |
| 5,079,352 | 1/1992 | Gelfand et al. | 536/27 |

FOREIGN PATENT DOCUMENTS

WO 93/23568  11/1993  WIPO.

OTHER PUBLICATIONS

Garrad et al.Infection and Immunity 62: 5027–5031 1994.
Xuan et al. Molecular and Cellular Biology 10: 4795–4806 1990.
Garrad and Bhattacharjee J. of Biology 174: 7379–7384 1992.
Ford et al. J. of Basic Microbiology 33: 179–186 1993.
Rothwell, in Understanding Genetics: A Molecular Approach 1993.
Musial, et al., Fungal Infections of the Immunocompromised Host: Clinical and Laboratory Apsects, Clin. Microbiol. Rev. 1:349–364 (1988).
Hopfer, R.L., et al., Detection and differentation of fungi in clinical specimens using polymerase chain reaction (PCR) amplification and restriction enzyme analysis, J. Med. Vet. Pharm. 31:65–75 (1993).
Buchman, T.G., et al., Detection of surgical pathogens by *in vitro* DNA amplification. Part I, Rapid identification of *Candida albicans* by *in vitro* amplification of a fungal specific gene. Surgery, 108:338–347 (1990).
Bhattacharjee, The α–aminoadipate Pathway for the Biosynsethesis of Lysine in Lower Eukaryotes, CRC Critical rev. in Microbiol. 12:131–151 (1985).
Lejohn, Enzyme Regulation, Lysine Pathways and Cell Wall Structures as Indicators of Major Lines of Evolution in Fungi, Nature 231:164–168 (1971).
Vogel, Two Modes of Lysine Synthesis Among Lower Fungi: Evolutionary Significance, Biochim. Biophys, Acta 41:172–174 (1960).
Garrad and Bhattacharjee, Lysine biosynthesis in selected pathogenic fungi: Characterization of lysine auxotrophs and the cloned LYS1 gene of *Candida albicans,* J. Bacteriol. 174:7379–7384 (1992).
Garrard, R., et al. (1994), "Molecular and Functional Analysis of the *LYS1* Gene of *Candida albicans,*" Infection and Immunity, vol. 62., No. 11, pp. 5027–5031.
Goshorn, A.K., et al. (1992), "Gene Isolation by Complementation in *Candida albicans* and Applications to Physical and Genetic Mapping," Infection and Immunity, vol. 60, No. 3, pp. 876–884.
Xuan, J.W. et al., (1990), "Overlapping Reading Frames at the *LYS5* Locus in the Yeast *Yarrow lipolytica,*" Molecular and Cellular Biology, vol. 10, No. 9, pp. 4795–4806.
Database Medline, A.N. 930554354, XP002021825 (1992).

*Primary Examiner*—Jeffrey Fredman
*Attorney, Agent, or Firm*—McDonnell, Boehnen, Hulbert & Berghoff

[57] ABSTRACT

The present invention provides novel methods and materials for detecting the presence of a fungus in a biological sample. The inventive methods and materials exploit the fact that the amino acid sequence of the saccharopine dehydrogenase molecule is highly conserved in fungi. Inventive hybridization probes, nucleic acids, PCR primers, antibodies, epitopes, reagents and methods are provided.

22 Claims, 20 Drawing Sheets

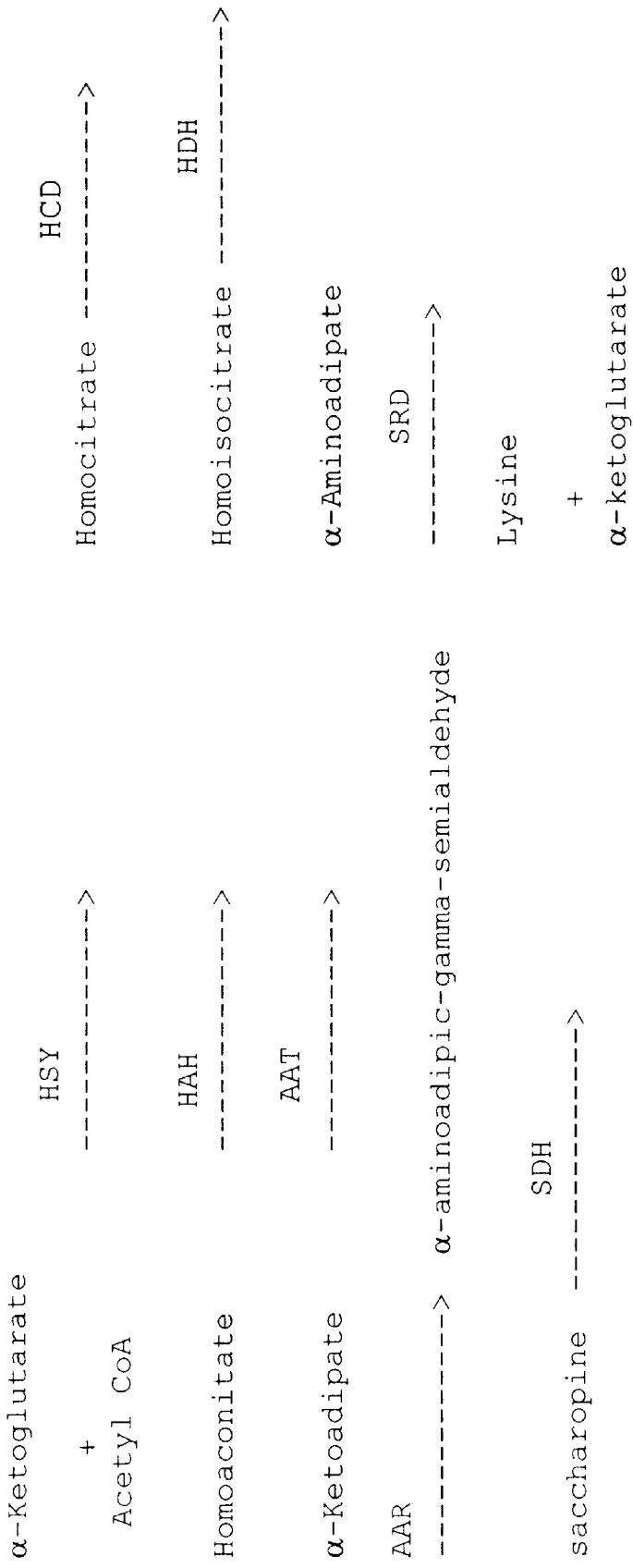

FIG. 2a

```
         BamHI             EcoRI
          /                 /
      CTAGTGGATCCCCCGGGCTGCAGGAATTCTTCTTCTTTTCTCCGTCTGAC
  1   ---------+---------+---------+---------+---------+
      GATCACCTAGGGGGCCCGACGTCCTTAAGAAGAAGAAAAGAGGCAGACTG

TCATTTTAATCGTCTGGTGGCTGGTGGCTGGTGGCTGGGGGCGGCACGGG
 51   ---------+---------+---------+---------+---------+
      AGTAAAATTAGCAGACCACCGACCACCGACCACCGACCGCCGCCGTGCCC

CAGCGGCAGCGGTGATGAGTGTGAGTTCCTTAATTATCGCCGCATGTTAT
101   ---------+---------+---------+---------+---------+
      GTCGCCGTCGCCACTACTCACACTCAAGGAATTAATAGCGGCGTACAATA

TACTCACTCACTCACAAACACTTTAGACGGAATTATCTCTGTCTCTCTCT
151   ---------+---------+---------+---------+---------+
      ATGAGTGAGTGAGTGTTTGTGAAATCTGCCTTAATAGAGACAGAGAGAGA

CTCTGTCTCTCTCTCTTTCTCACTTAGAGAATATATAAACCACATTACAA
201   ---------+---------+---------+---------+---------+
      GAGACAGAGAGAGAGAAAGAGTGAATCTCTTATATATTTGGTGTAATGTT

TTCATTTATTCTACATTGAACAATTTGAATGAAAAAAAAAAAAACATTTT
251   ---------+---------+---------+---------+---------+
      AAGTAAATAAGATGTAACTTGTTAAACTTACTTTTTTTTTTTTGTAAAA

ATACCTTTACTTCTTACTTCTTTCTAATAATCAACTATACTAGCTAACTC
301   ---------+---------+---------+---------+---------+
      TATGGAAATGAAGAATGAAGAAAGATTATTAGTTGATATGATCGATTGAG

ATATACTAATTATGTCTAAATCACCAGTTATTCTTCATTTAAGAGCAGAA
351   ---------+---------+---------+---------+---------+
      TATATGATTAATACAGATTTAGTGGTCAATAAGAAGTAAATTCTCGTCTT
                     M  S  K  S  P  V  I  L  H  L  R  A  E

ACTAAACCATTAGAAGCTAGAGCTGCTTTAACTCCTTCTACTACTAAACA
401   ---------+---------+---------+---------+---------+
      TGATTTGGTAATCTTCGATCTCGACGAAATTGAGGAAGATGATGATTTGT
       T  K  P  L  E  A  R  A  A  L  T  P  S  T  T  K  Q
```

FIG. 2b

```
    ATTACTCGATGCTGGATT TGAAATTTATGTTGAAGAATCTTCTCAATCTA
451 ---------+---------+---------+---------+---------+
    TAATGAGCTACGACCTAAACTTTAAATACAACTTCTTAGAAGAGTTAGAT
     L  L  D  A  G  F  E  I  Y  V  E  E  S  S  Q  S  T

CTTTTGATATTAAAGAATATGAAGCTGTTGGTGCTAAAATAGTACCTGAA
501 ---------+---------+---------+---------+---------+
    GAAAACTATAATTTCTTATACTTCGACAACCACGATTTTATCATGGACTT
       F  D  I  K  E  Y  E  A  V  G  A  K  I  V  P  E

GGTTCATGGAAAACTGCTCCTAAAGAGAGAATTATTTTTGGTTTAAAAGA
551 ---------+---------+---------+---------+---------+
    CCAAGTACCTTTTGACGAGGATTTCTCTCTTAATAAAAACCAAATTTTCT
     G  S  W  K  T  A  P  K  E  R  I  I  F  G  L  K  E

ATTACCTGAAAATGAAACTTTCCCATTAATTCATGAACATATTCAATTTG
601 ---------+---------+---------+---------+---------+
    TAATGGACTTTTACTTTGAAAGGGTAATTAAGTACTTGTATAAGTTAAAC
     L  P  E  N  E  T  F  P  L  I  H  E  H  I  Q  F  A

CTCATTGTTATAAAGATCAAGCTGGTTGGCAAGATGTTTTAAAAAGATTC
651 ---------+---------+---------+---------+---------+
    GAGTAACAATATTTCTAGTTCGACCAACCGTTCTACAAAATTTTTCTAAG
       H  C  Y  K  D  Q  A  G  W  Q  D  V  L  K  R  F

CCACAAGGTAATGGTATATTATATGATTTAGAATTTTTAGAAAATGATCA
701 ---------+---------+---------+---------+---------+
    GGTGTTCCATTACCATATAATATACTAAATCTTAAAAATCTTTTACTAGT
     P  Q  G  N  G  I  L  Y  D  L  E  F  L  E  N  D  Q

AGGTAGGAGAGTTGCTGCCTTTGGATTTTATGCTGGATTTGCTGGGGCTG
751 ---------+---------+---------+---------+---------+
    TCCATCCTCTCAACGACGGAAACCTAAAATACGACCTAAACGACCCCGAC
       G  R  R  V  A  A  F  G  F  Y  A  G  F  A  G  A  A

CCATTGGGGTATTAGATTGGAGTTTTAAACAATTGAATGGTAATACTAAA
801 ---------+---------+---------+---------+---------+
    GGTAACCCCATAATCTAACCTCAAAATTTGTTAACTTACCATTATGATTT
       I  G  V  L  D  W  S  F  K  Q  L  N  G  N  T  K

GGTACTAAAGGTGAAGGTGAAGGTGGTGAATTACCTGGGGTGACTCCATA
851 ---------+---------+---------+---------+---------+
    CCATGATTTCCACTTCCACTTCCACCACTTAATGGACCCCACTGAGGTAT
     G  T  K  G  E  G  E  G  G  E  L  P  G  Y  T  P  Y
```

FIG. 2c

```
                                                          HindIII
                                                         /
         TCCTAATGAAAATGAATTAATTAAAGATGTTAAAATTGAATTAGAAAAAG
  901    ---------+---------+---------+---------+---------+
         AGGATTACTTTTACTTAATTAATTTCTACAATTTTAACTTAATCTTTTTC
           P  N  E  N  E  L  I  K  D  V  K  I  E  L  E  K  A CTTTAACTAAAAATGGGGGTCAATATCCTAAATGTCTTGTTATTGGTGCC
  951    ---------+---------+---------+---------+---------+
         GAAATTGATTTTTACCCCCAGTTATAGGATTTACAGAACAATAACCACGG
           L  T  K  N  G  G  Q  Y  P  K  C  L  V  I  G  A TTGGGTAGATGTGGATCTGGTGCCATTGATTTATTTAAAAAAATTGGTAT
 1001    ---------+---------+---------+---------+---------+
         AACCCATCTACACCTAGACCACGGTAACTAAATAAATTTTTTAACCATA
           L  G  R  C  G  S  G  A  I  D  L  F  K  K  I  G  I CCCTGATGATAATATTGCTAAATGGGATATGGCTGAAACTGCTAAAGGTG
 1051    ---------+---------+---------+---------+---------+
         GGGACTACTATTATAACGATTTACCCTATACCGACTTTGACGATTTCCAC
           P  D  D  N  I  A  K  W  D  M  A  E  T  A  K  G  G GTCCATTCCAAGAAATTGTTGATCTGGATATTTTCATTAATTGTATTTAT
 1101    ---------+---------+---------+---------+---------+
         CAGGTAAGGTTCTTTAACAACTAGACCTATAAAAGTAATTAACATAAATA
           P  F  Q  E  I  V  D  L  D  I  F  I  N  C  I  Y TTATCTAAACCAATCCCACCATTTATTAATAAAGAAATTTTGAATAATGA
 1151    ---------+---------+---------+---------+---------+
         AATAGATTTGGTTAGGGTGGTAAATAATTATTTCTTTAAAACTTATTACT
           L  S  K  P  I  P  P  F  I  N  K  E  I  L  N  N  E AAATAGAAAATTGACTACTATTGTTGATGTTTCTGCTGATACTACTAATC
 1201    ---------+---------+---------+---------+---------+
         TTTATCTTTTAACTGATGATAACAACTACAAAGACGACTATGATGATTAG
           N  R  K  L  T  T  I  V  D  V  S  A  D  T  T  N  P CTCATAATCCAATCCCAGTATATGAAATTGCTACAGTTTTCAATGAACCA
 1251    ---------+---------+---------+---------+---------+
         GAGTATTAGGTTAGGGTCATATACTTTAACGATGTCAAAAGTTACTTGGT
           H  N  P  I  P  V  Y  E  I  A  T  V  F  N  E  P
```

FIG. 2d

```
       ACCGTTGAAGTTAAACTTGATAAAGGTCCTAAATTATCAGTATGTTCAAT
1301   ---------+---------+---------+---------+---------+
       TGGCAACTTCAATTTGAACTATTTCCAGGATTTAATAGTCATACAAGTTA
        T  V  E  V  K  L  D  K  G  P  K  L  S  V  C  S  I

HindIII
                              /
       TGATCATTTACCTTCTTTATTACCTAGAGAAGCTTCAGAATTTTTTGCTA
1351   ---------+---------+---------+---------+---------+
       ACTAGTAAATGGAAGAAATAATGGATCTCTTCGAAGTCTTAAAAAACGAT
          D  L  M  P  S  L  L  E  L  P  N  R  D  T  S  P AAGATTTAATGCCATCATTATTGGAATTACCAAATAGAGATACTTCTCCA
1401   ---------+---------+---------+---------+---------+
       TTCTAAATTACGGTAGTAATAACCTTAATGGTTTATCTCTATGAAGAGGT
          D  L  M  P  S  L  L  E  L  P  N  R  D  T  S  P GTATGGGTTAGAGCTAAACAATTATTTGATAAACACGTTGCCAGACTTGA
1451   ---------+---------+---------+---------+---------+
       CATACCCAATCTCGATTTGTTAATAAACTATTTGTGCAACGGTCTGAACT
        V  W  V  R  A  K  Q  L  F  D  K  H  V  A  R  L  D TAAAGAGTAGTAGTAGGTTTACAAGTCAAGTAAATGTGTTTAATAAATAT
1501   ---------+---------+---------+---------+---------+
       ATTTCTCATCATCATCCAAATGTTCAGTTCATTTACACAAATTATTTATA
        K  E  *  *  *

Poly A
                     **************                           ***
       TTTATTAAATCTTTTATTTTATTTTATTTCATTTCATTTCTTAATTAGTA
1551   ---------+---------+---------+---------+---------+
       AAATAATTTAGAAAATAAAATAAAATAAAGTAAAGTAAAGAATTAATCAT

****
       TCTGTGTATATTGGGATCTATTAGTAAAATAGTAGCACTATTATTATTCT
1601   ---------+---------+---------+---------+---------+
       AGACACATATAACCCTAGATAATCATTTTATCATCGTGATAATAATAAGA

***
       AATGTTACACTAACTTTTCTTTTCTTTTAATATTATTCTTTTTTGATTT
1651   ---------+---------+---------+---------+---------+
       TTACAATGTGATTGAAAAGAAAAGAAAAATTATAATAAGAAAAAACTAAA
```

FIG. 2e

```
                                                PolyA
                                              * * * * * *
      CTTACCCTTTTTATTCTTTTCACCTTGCATTATATTTTTAATTTCTTCAC
1701  ---------+---------+---------+---------+---------+
      GAATGGGAAAAATAAGAAAAGTGGAACGTAATATAAAAATTAAAGAAGTG EcoRV     HindIII      SalI
                                        /       /              /
      CATCAGTTTCATATTCAGATTCACTAGGGATATCAAGCTTATCGATACCG
1751  ---------+---------+---------+---------+---------+
      GTAGTCAAAGTATAAGTCTAAGTGATCCCTATAGTTCGAATAGCTATGGC

TCGACC
1801  ------ 1806
      AGCTGG
```

FIG. 3a

```
                 1   MSKSPVILHL  RAETKPLEAR  AALTPSTTKQ  LLDAGFEIYY
C. albicane          ..MAAVTLHL  RAETKPLEAR  AALTPTTVKK  LIAKGFKIYV
S. cerevisiae        .MTAPVKLHL  RAETKPLEHR  SALTPTTTRR  LLDAGFEVFV
Y. lipolytica        ..........  ..........  ..........  ..........
C. neoformane        ..........  ..........  ..........  ..........
Consensus            ----------  ----------  ----------  ----------

41   EESSQSTFDI  KEYEAVGAKI  VPEGSWKTAP  DERIIFGLKE
C. albicane          EDSPQSTFNI  NEYRQAGAII  VPAGSWKTAP  RDRIIIGLKE
S. cerevisiae        EKSPLRIFDD  QEFVDVGATL  VEEGSWVSAP  EDRMIGLKE
Y. lipolytica        ..........  ..........  ..........  ..........
C. neoformane        ..........  ..........  ..........  ..........
Consensus            ----------  ----------  ----------  ----------

81   LPENETFPLI  HEHIQFAHCY  KDQAGWQDVL  KRFPQGNGIL
C. albicane          MPETDTFPLV  HEHIQFAHCY  KDQAGWQNVL  MRFIKGAGTL
S. cerevisiae        LPE.ESFPLS  HEHIQFAHCY  KDQGGWQDVL  SRFPAGNGTL
Y. lipolytica        ..........  HEHIQFAHCY  KDQAGWQDVL  RRFAQGKGTL
C. neoformane        ----------  HEHIQFAHCY  K-Q-GW--VL  -RF--G-G-L
Consensus 121   YDLEFLENDQ  G.RRVAAFGF  YAGFAGAAIG  VLDWSFKQLN
C. albicane          YDLEFLENDQ  G.RRVAAFGF  YAGFAGAALG  VRDWAFKQ..
S. cerevisiae        YDLEFLEDDN  G.RRVAAFGF  HAGFAGAAIG  VETWAFQQ..
Y. lipolytica        YDLEFLEDPV  SHRRVAAFGF  HAGFAGAAAG  ALAFAAQQ..
C. neoformane        YDLEFLE---  --RRVAAFGF  --AGFAGAA-G  ------Q--
Consensus            ----------  ----------  ----------  ----------
```

FIG. 3b

```
     161
C. albicane    GNTKGTKGEG  EGGELPGVTP  YPNENELIKD  VKIELEKALT
S. cerevisiae  .......THS  DDEDLPAVSP  YPNEKALVKD  VTKDYKEALA
Y. lipolytica  .......THP  DSENLPGVSP  YPNETLLVDK  IKKDLAAAVE
C. neoformane  .......TQN  GQGKLGELKP  YPENGEMVKE  VSEALEG..T
Consensus      ----------  ------L---  YPEN------  ----------

201
C. albicane    KNGGQYPKCL  VIGALGRCGS  GIADLFKKIG  IPDDNIAKWD
S. cerevisiae  .TGARKPTVL  IIGALGRCGS  GIADLLHKVG  IPDANILKWD
Y. lipolytica  K.GSKLPTVL  VIGALGRCGS  GIADLARKVG  IPEENIIRWD
C. neoformane  KEGKKGVKVL  IIGALGRCGS  GAVDLFRKAG  VAEENIVKWD
Consensus      --G------L  -IGALGRCGS  GA-DL--K-G  ----NI--WD 241
C. albicane    MEATAKGGPF  QEIVDLDIFI  NCIYLSKPIP  PFINKEILNN
S. cerevisiae  IKETSRGGPF  DEIPQADIFI  NCIYLSKPIA  PFTNMEKLNN
Y. lipolytica  MNETKKGGPF  QEIADADIFI  NCIVLSQPIP  PFINYDLLNK
C. neoformane  MAETAKGGPF  PEILDVDIFI  NC........  ..........
Consensus      --ET--GGPF  -EI---DIFI  NC--------  ----------

281
C. albicane    ENRKLTTIVD  VSADTTNPHN  PIPVYEIATV  FNEPTVEVKL
S. cerevisiae  PNRRLRTVVD  VSADTTNPHN  PIPIYTVATV  FNKPTVLVPT
Y. lipolytica  ETRKLSVIVD  VSADTTNPHN  PVPVYTIATT  FDHPTVPVET
C. neoformane  ..........  ..........  ..........  ..........
Consensus      ----------  ----------  ----------  ----------
```

FIG. 3c

```
                    321
C. albicane             DKGPKLSVCS  IDKLPSLLPR  EASEFFAKDL  MPSLLELLPNR
S. cerevisiae           TVGPKLSVIS  IDKLPSLLPR  EASEFFSHDL  LPSLELLPQR
Y. lipolytica           TAGPKLSVCS  IDKLPSLLPR  EASEAFSEAL  LPSLLQLPQR
C. neoformane           ..........  ..........  ..........  ...........
Consensus               ----------  ----------  ----------  -----------

361
C. albicane             DTSPVWVRAK  QLFDKHVARL  DKE....
S. cerevisiae           KTAPVWVRAK  KLFDRH CARV  KRSSRL
Y. lipolytica           DTAPVWTRAK  ALFDKHVLRI  GE.....
C. neoformane           ..........  ..........  .......
Consensus               ----------  ----------  -------
```

FIG. 5a

```
 372 CACCAGTTATTCTTCATTTAAGAGCAGAAACTAAACCATTAGAAGCTAGA  421
     ||||||||  |||| ||| || || ||| ||||||| ||||||||||||
1757 CACCAGTGAAGCTCCATCTCCGAGACCCGAGCCTCGAGCACCGA        1708

422 GCTGCTTTAACTCCTTCTACTACTAAACAATTACTCGATGCTGGATTTGA  471
     |||||||||||  | |||  || ||| |||| |||||||||||||||||
1707 TCTGCTCTCCACGCCTACTACCACCCGAAAGCTGCTTGATGCTGGATTCGA 1658

472 AATTTATGTTGAAGAATCTTCTCAATCTACTTTTGATATTAAAGAATATG  521
     | || | || ||||| |||||||||||||||||||||||||||||||||
1657 GGTCTTTGTGGAGAAGTCTTCTCAATCTACTTTTGATATTAAAGAATATG 1608

522 AAGCTGTTGGTGCTAAAAATAGTACCTGAAGGTTCATGGAAAACTGCTCCT  571
     ||||||| || ||| ||||| || ||||||||||||| ||| ||| || |
1607 TCGATGTCGGAGCCCACTCTTGTCGAGGAGGGCTCTTGGGTCTCTGCCCCC 1658

572 AAAGAGAGAATAATTTTTGGTTTAAAAGAATTACCTGAAAATGAAACTTT  621
     || |||||||||| ||||| ||||||| |||| ||||||   ||| |||
1557 GAGGACCGAATGATTATTGGTCTTAAGGAGCTGCGTG... AGGAATCTTT 1511

622 CCCATTAAATTCATGAACATATTCAATTTGCTTCATTGTTATAAAGATCAAG  671
     |||| |  ||||||||||| ||| ||| || ||||||  | ||||||| |||
1510 CCCTCTGTCTCACGAGCACATCCAGTTTGCTCAGTGCTACAAGGATCAGG 1461
```

FIG. 5b

```
 672   CTGGTTGGCAAGATGTGTTTTAAAAAGATTCCCACAAGGTAATGGTATATTA    721
         ||| ||||  ||| |  |  |||  | ||  |  ||||||| || | |
1460   GCGGATGGAAGGACGTTCTGAGCCGATTCCCCGCAGGAAACGGAACTCTG    1411

722   TATGATTTAGAATTTTTAGAAAATGATCAAGGTAGGAGAGTTGCTGCCTT    821
        |||||| || |   |  ||||||||  ||||||||||  ||||||| ||
1410   TACGACCTTGAGTTCCTGGAGGATGACAATGACGACGAGTTGCCGCCTT    1361

772   TGGATTTTATGCTGGATTTGCTGGGGCTGCCATTGGGGTATTAGATTGGA    821
        |||| ||| ||||| ||| || | ||||||||| || ||| |||||||
1360   TGGCTTCCACGCTGGATTCGCCGGTGTAATACTAAAGGTACTCGGTCGAGACTTGGG    1311

822   GTTTTAAACAATTGAATGGTAATACTAAAGGTACTCGGTGTCGGTGTCGAGACTTGGG    871
       ||  ||   |                                       ||||||||||
1310   CCTTCCAGCA..........................GACCCACCCCGACAGCGAA    1282

872   GGTGGTGAATTACCTGGGGTGACTCCATATCCTAATGAAAATGAATTAAT    921
        |||||||||||  |||||||||||||| |||| ||||||||||||| ||
1281   ......AACCTGCCCGGTGTCTCTGCCTATCCCCAATGAGACCGAGCTTGT    1238

922   TAAAGATGTTAAAATTGAATTAGAAAAAGCTTTAACTAAAAATGGGGGTC    971
        |||||||| ||| ||  || ||| ||| |   ||| |||| |||||||
1237   CGACAAGATTAAGAAGGATCTTGCCGCTGCT.....GTTGAGAAGGGCTCC    1192
```

FIG. 5c

```
 972 AATATCCTAAAATGT.CTTGTTATTGGTGCCTTGGGTAGATGTGGATCTGG 1020
         ||  |||||||||  ||||||||  ||||  ||| || |||||||||
1191 AAGCTCCCTACCGTCCCTGGTGATTGGTGCTCTTGGCCGATGTGGATCCGG 1142

1021 TGCCATTGATTTATTTAAAAAATTGGTATCCCTGATGATAATATTGCTA 1072
     ||||||||||||  || |   |   ||||||||||| ||| |||| |||
1141 TGCCATTGATCTGGGCCCCGAAAGGTCGGTATCCCCGAAGAGAACATCATTC 1092

1071 AATGGGATATGGCTGAAACTGCTAAAGGTGGTCCATTCCAAGAAATTGTT 1120
     ||||| || |||||||| | || ||||| |  |||||||||| |||||
1091 GATGGGACATGAACGAGACCAAGAAGGGTGACCCTTCCAAGAGATTGCT 1170

1121 GATCTGGATATTTCATTAATTGTATTTATTTATCTAAACCAATCCCACC 1170
     ||| |||||||| ||| | | |||| |   ||| |||||||| | ||
1041 GACGCGGATATCTTCATCAACTGCATCTACCTGTCTCAGCCCATTCCTCC 992

1171 ATTTATTAATAAAAGAAATTTTGAATAATGAAAAATAGAAAAATTGACTACTA 1220
      ||| | | |||| |||   |  |  | |||||  ||| |||| |||| |
 991 TTTCATCAACTACGATCTGCTCAACAAGGAGACCCGAAAGCTCAGTGTCA 942

1221 TTGTTGATGTTTCTGCTGATACTACTAATCCTCATAATCCCAGTA 1270
     |||| || ||||| |||||  |  ||  ||  |  |||||||| |
 941 TTGTCGACGTCTCTGCTGACACCACCAACCCCTGTCCCCGTG 892
```

FIG. 5d

```
1271  TATGAAATTGCTACAGTTTTCAATGAACCAACCGTTGAAGTTAAACTTGA  1320
      ||  |||||||||||| |||   |||  |||   ||||||||||
 891  TACACAATTGCTACCACGTTCGACCATCCCACCGTGCCTGTTGAGACCAC   842

1321  TAAAGGTCCTAAATTATCAGTATGTTCAATTGATCATTACCTTCTTTAT  1370
      |  ||  ||||| |  ||| | || ||   || ||  || ||| | |
 841  TGCTGGCCCCAAGCTGTCCGTGCCTCGATCGACCACCTGCCCCTCTCTTC   792

1371  TACCTAGAGAAGCTTCAGAATTTTTGGTAAAGATTTAATGCCATCATTA  1420
       || |||| || |  |  | | | ||| |||  |||  |||| || ||
 791  TGCCGGAGAGGCTTCCGAGGCGTTTTCTGAGGCTCTGCTGCCTTCTCTG   742

1421  TTGGAATTACCAAATAGAGATACTTCTCCAGTATGGGTTAGAGGTAAACA  1470
       |||| |||||  |  ||||| |  || |||||||   |||||||
 741  CTGCAGCTTCCTCAGCGAGACACTGCTCCCTGTCTGGACCCGACTTAAGGC   692

1471  ATTATTTGATAAACACGTTGCCAGACTTG  1499
       |||  ||  |||||||| |    |||
 691  TCTGTTCGACAAACACGTTCTGCGAATTG   663
```

FIG. 6a

```
                       10         20         30
            CTTGTTATTGGTGCCTTGGGTAGATGTGGATCTG
            ||||||||||||  |||||||  ||||  |||||  ||
CCACCGGGGCCAGAAAGCCAACCGTGTTAATCATTGGTGCGCTAGGAAGATGTGGTTCCG
   570        580        590        600        610        620

40         50         60         70         80         90
GTGCCATTGATTTATTTATTTAAAAAAATTGGTATCCCTGATGATAATATTGCTAAATGG
|||||||||||||  |||  ||  |   |||||  |||||||||||    |||||   ||
GTGCCATCG----ATCTGTTGCACAAAGTTGGTATTCCAGATGCTAACATATTAAAAATGG
   630        640        650        660        670

100        110        120        130        140
GATAT-----GGCTGCTAAAGGTGGTCCATTCCAAGAAATTGTTGATCTGGATATTTC
|||||     |  |||  |||||||  ||||||||||| |||||||||||||||||||
GATATCAAAGAAAACTTCCCGTGGTGGTCCCTTTGACGAAATTCCACAAGCTGATATTTC
   680        690        700        710        720        730

150        160        170        180        190        200
ATTAATTGTATTTATTTATCTAAACCAATCCCACCATTTATTAATAAAGAAATTTGAAT
||  |||||||||||| |||||  ||  ||  |||||||||  ||||||||||||||||
ATCAATTGTATATCTATCGAAGCCAATTGCTCCTTTCACTAACATGGAGAAACTGAAT
   740        750        760        770        780        790
```

FIG. 6b

```
210         220         230         240         250         260
AATGAAAAATAGAAAAATTGACTACTATTGTTGATGTTTCTGCTGATACTACTAATCCTCAT
||| || ||||| ||  | ||||| ||  |||| || |||| || ||||  |  ||
AATCCTAACAGAAGACTAAGGACCGTGGTGGACGTATCAGCAGACACTACCAACCCCTCAC
800         810         820         830         840         850

270         280         290         300         310         320
AATCCCAATCCCAGTATATGAAAATTGCTACAGTTTTCAATGAACCAACCGTTGAAGTTAAA
|| ||| |||   |||||   |||   || || ||||| |  ||||| ||||| ||||
AACCCCATCCCAATATACACTGTGGCTACTGTGTTTAACAAACCTACCGTTCTGGTACCT
860         870         880         890         900         910
```

FIG. 7 cont.

```
304  VYEIATVFNEPTVEVKLDKGPKLSVCSIDHLPSLLPREASEFFAKDLMPS  353
     ||·|||·|::·|||·|·   ||||||||||||||||||||·|···|:||
292  VYTIATTFDHPTVPVETTAGPKLSVCSIDHLPSLLPREASEAFSEAALLPS  341

354  LLELPNRDTSPVWVRAKQLFDKHVAR  379
     ||:||·|||·|||·|||·||||||·|
342  LLQLPQRDTAPVWTRAKALFDKHVLR  367
```

FIG. 8

```
  1  GGGATCCGCC  CACGAGCACA  TCCAGTTTGC  CCACTGCTAC  AAGCAACAGG
     vector
 51  CCGGATGGAA  TGACGTCCTC  CGCCGATTCG  CCAGGGCAA   GGGTACCCTC
101  TACGACCTCG  AATTCCTCGA  AGACCCCGTT  TCCCACCGAC  GTGTCGCCGC
151  ATTCGGTTTC  CACGCCGGTT  TCGCCGGGCGC GCCCGCTGGT  GCCCTCGCCT
201  TTGCCGCTCA  GCAAACCCAA  AATGGGCAAG  GCAAGCTGGG  CGAATTGAAG
251  CCGTACCCCA  ATGAAGGCGA  AATGGTCAAG  GAAGTGAGTG  AGGCGTTGGA
301  GGGCACCAAG  GAAGGGAAGA  AGGGAGTAAA  GGTTTTGATC  ATTGGAGCCT
351  TGGGACGATG  TGGATCCGGT  GCGGTTGACC  TCTTCCGGAA  GGCCGGCGTT
401  GCCGAGTACG  TCTTTTTGTC  CTCTCTCTCC  CCTCTTGATC  ATCTTGCTCA
                                        ------intron---------
451  CGTCTTCTCG  GCAAAATAGG  GAAAATATCG  TCAAGTGGGA  TATGCCCGAG
502  ACCGCCAAGG  GCGGTCCCTT  CCCCGAAATC  CTGGACGTCG  ACATTTTCAT
551  CAACTGCATG  GGCTAGA
                vector
```

METHODS AND REAGENTS FOR DETECTING FUNGAL PATHOGENS IN A BIOLOGICAL SAMPLE

BACKGROUND OF THE INVENTION

1. Field of the Invention

The present invention relates to novel methods for identifying fungal pathogens in a biological sample. In particular, this invention relates to methods for screening biological samples for the presence of fungal pathogens using hybridization methods and probes capable of sensitively and specifically detecting and distinguishing nucleic acid sequences unique to fungi. Also provided are antibodies capable of binding selectively to fungal proteins.

2. Background of the Invention

*Candida albicans*, once considered a relatively minor fungal pathogen, has recently become a particularly serious health concern as the causative agent of candidosis (also called candidiasis). The incidence of *C. albicans* infections is rising rapidly with the increase in immune deficiency diseases and immunosuppressive therapy (Bodey and Fainstein, In *Systemic Candidiasis*, pp. 135 (Eds., Raven Press, New York 1985). Candidosis is a common nosocomial infection afflicting both immunosuppressed and post-operative patients. (Holmes, A. R., et al. Yeast-specific DNA probes and their application for the detection of *Candida albicans*, J. Med. Microbiol., 37:346–351 (1992)). Although candidosis is a particular concern among immunocompromised individuals, Candida infections are not limited to this group. *C. albicans* is the major opportunistic fungal pathogen in humans (Odds, F. C., In *Candida and candidosis*, (Ed.) Leicester University Press, Leicester, United Kingdom (1989)) and is capable of establishing infection whenever the host immune system or normal flora are perturbed.

Although the *C. albicans* species is a particular health concern, other species of the Candida genus are also pathogenic. The genus Candida is comprised of approximately 200 diverse yeast species classified together due to their lack of a sexual cycle (Meyer et al., In Genus 4, Candida, pp. 1–12, (Ed.) N. J. W. Kregervan Riij, Elsevier, Amsterdam (1984)). A minority of Candida species are pathogenic and 80% of the clinical isolates are either *C. albicans* or *C. tropicalis* (Hopfer, R. L. In Mycology of Candida Infections, G. P. Bodey, and V. Fainstein (eds.), Raven Press, New York (1985)).

In immunocompromised hosts, candidosis is a life threatening condition. The prognosis for a patient infected with *C. albicans* can be improved markedly, however, with prompt antifungal treatment. Treatment may be delayed until a positive diagnosis of Candidosis is obtained since antifungal drugs are toxic. See Holmes, et al., 1992.

Diagnostic tests for the identification of *C. albicans* or other fungal pathogens in vivo often require complete cultural identification protocols (Musial et al., Fungal Infections of the Immunocompromised Host: Clinical and Laboratory Aspects, Clin. Microbiol. Rev. 1:349–364 (1988)). Methods currently used for the diagnosis of fungal pathogens include: cultural identification, biopsy, serodiagnosis, identification of metabolites, isoenzyme determination, pulsed field gel electrophoresis and analysis of restriction fragment length polymorphisms. Most of these methods are time consuming, laborious and provide inconclusive results. Serodiagnosis is particularly unacceptable for the identification of candidosis, as most individuals have been exposed to Candida and therefore have circulating antibodies against Candida even in the absence of infection. Thus, serodiagnosis can only be accomplished by determining a rise in the titer for anti-Candida antibodies as compared to the titer present in the non-disease state. Such titers are generally unavailable, rendering the technique of serodiagnosis less attractive for the diagnosis of Candida infection.

Potential methods for diagnosing fungal infections through DNA screening have focused on detecting specific nucleotide sequences such as ribosomal DNA (Hopfer, R. L. et al., Detection and differentiation of fungi in clinical specimens using polymerase chain reaction (PCR) amplification and restriction enzyme analysis, J. Med. Vet. Pharm. 31:65–75 (1993)) and the $P_{450}$ genes (Buchman, T. G. et al., Detection of surgical pathogens by in vitro DNA amplification. Part I, Rapid identification of *Candida albicans* by in vitro amplification of a fungal specific gene. Surgery, 108:338–347 (1990)). However, no commercial diagnostic techniques embodying methods related to the identification of these genes in biological samples are known.

One impediment to developing nucleic acid based screening techniques for Candidosis is that basic information about uniquely fungal metabolic pathways and cognate genes of *C. albicans* is lacking (Kurtz et al., Molecular Genetics of *Candida albicans*, pp. 21–73, Kirsch, Kelly and Kurtz (eds.) CRC Press Inc. Boca Raton, Fla. (1990)). The sequences of approximately forty *C. albicans* genes are available in computerized databases, and very few are involved in amino acid biosynthesis. The relatively small database of genetic information available for *C. albicans* places limitations upon the number of DNA sequences that can be used as targets for screening probes and concomitantly reduces the likelihood of identifying a sequence unique to fungi and amenable to identification through DNA screening techniques. For example, very few of these genes are involved in amino acid biosynthesis.

Similar impediments exist to developing immunological methods of identifying a fungus present in a biological sample. Relatively few antigenic determinants unique to fungi are known, and none are believed to have been successfully utilized as targets for antibody binding in commercially available form.

Among the proteins that have been studied in *C. albicans* and other pathogenic fungi are the enzymes that make up the α-aminoadipate pathway for the biosynthesis of lysine. This unique pathway has been identified in Phycomycetes, Euglenids, yeasts and other higher fungi (Bhattacharjee, The α-aminoadipate Pathway for the Biosynthesis of Lysine in Lower Eukaryotes, CRC Critical Rev. in Microbiol. 12:131–151 (1985); Lejohn, Enzyme Regulation, Lysine Pathways and Cell Wall Structures as Indicators of Evolution in Fungi, Nature 231:164–168 (1971); and Vogel, Two Modes of Lysine Synthesis Among Lower Fungi: Evolutionary Significance, Biochim. Biophys. Acta 41:172–174 (1960)) and is present in *C. albicans* and other pathogenic fungi (Garrad, R. Masters Thesis, Miami University (1989) and, Garrad and Bhattacharjee, Lysine biosynthesis in selected pathogenic fungi: Characterization of lysine auxotrophs and the cloned LYS1 gene of *Candida albicans*, J. Bacteriol. 174:7379–7384 (1992)). Lysine is an essential amino acid for humans and animals and is synthesized by the diaminopimelic acid pathway in bacteria and plants. The α-aminoadipate pathway consists of eight enzyme catalyzed steps; there appear to be seven free intermediates in *S. cerevisiae* (Bhattacharjee, The α-aminoadipate pathway for the biosynthesis of lysine in lower eukaryotes, CRC Critical Review in Microbiol. 12:131–151 (1985)). The final reversible step of the α-aminoadipate pathway is catalyzed by saccharopine dehydrogenase (EC 1.5.1.7), which is encoded by the LYS1 gene of *S. cerevisiae* and *C. albicans*, and the LYS5 gene of *Y. lipolytica* (Fujioka, Chemical mechanism of saccharopine dehydrogenase (NAD, L-lysine forming) as deduced from initial rate pH studies, Arch. Biochem. Biophys. 230:553–559 (1984); Garrad and Bhattacharjee, Lysine biosynthesis in selected pathogenic fungi: Characterization of lysine auxotrophs and the cloned LYS1 gene of *Candida albicans*, J. Bacteriol. 174:7379–7384 (1992); and Xuan et al., Overlapping reading frames at the LYS5 locus in the yeast *Yarrowia lipolytica*, Mol. Cell. Biol. 10:4795–4806 (1990)).

SUMMARY OF THE INVENTION

The present invention provides nucleic acid probes having nucleotide sequences that code for polypeptides that are (a) derived from saccharopine dehydrogenase expressed by wild type *Candida albicans* and (b) conserved among fungi, wherein the nucleic acid probes are not homologous to and do not cross react with nucleotide sequences found in the human genome. The invention also encompasses homologues of such nucleic acid probes. Additionally, the invention relates to methods for using such probes to screen biological samples for the presence of fungal pathogens. Furthermore, the invention provides a rapid method for identifying a fungus in a biological sample based on the use of monoclonal antibodies raised to unique fungal epitopes of saccharopine dehydrogenase expressed by wild type *Candida albicans*.

The demand for methods for the rapid, sensitive and selective detection of fungal pathogens in biological samples and particularly for such detection of *Candida albicans* in biological samples increases each year. The increasing use of immunosuppressive drugs in connection with organ transplants, autoimmune diseases and cancer, taken together with the increasing number of patients suffering from acquired immunodeficiency syndrome, have resulted in a dramatic increase in the incidence of candidosis and other fungal infections. Because fungal infections are life threatening, physicians may prescribe antifungal drugs even in the absence of a definitive diagnosis. Due to the sometimes toxic effects of such drugs, however, their administration without such a definitive diagnosis is undesirable.

In a first aspect, this invention provides nucleic acid hybridization probes, each having a nucleotide sequence selected from the group consisting of nucleic acid sequences that code for polypeptides that are (a) derived from saccharopine dehydrogenase expressed by wild type *Candida albicans* and (b) conserved among fungi, wherein the nucleic acid hybridization probes are not homologous to and do not cross hybridize with nucleotide sequences found in the human genome. Homologues of such probes are also contemplated by the present invention. Examples of polypeptides derived from saccharopine dehydrogenase and conserved among fungi include the following:
LHLRAETKPLE (SEQ ID: 1)
LLDAGFE (SEQ ID: 2)
GLKELPE (SEQ ID: 3)
HEHIQFA (SEQ ID: 4)
LYDLEFLE (SEQ ID: 5)
GRRVAAFGF (SEQ ID: 6)
AGFAGAAIGV (SEQ ID: 7)
LVIGALGRCGSGAIDL (SEQ ID: 8)
KGGPFQEI (SEQ ID: 9)
DIFINCI (SEQ ID: 10)
IVDVSADTTNPHNP (SEQ ID: 11)
GPKLSVCSIDHLPSLLPREASE (SEQ ID: 12)
LFDKHVAR (SEQ ID: 13)

Homologues and portions of such probes are also contemplated by the present invention. For purposes of the present invention, a "portion of a probe" shall be taken to mean a probe coding for an amino acid sequence that is a truncated version of one of the sequences provided set forth above.

In a preferred aspect, this invention provides nucleic acid hybridization probes selected from the group consisting of nucleotide sequences that code for the following polypeptides derived from saccharopine dehydrogenase:
LVIGALGRCGSGAIDL (SEQ ID: 1)
GPKLSVSIDHLPSLLPREASE (SEQ ID: 2)
DIFINCI (SEQ ID: 10) or
HEHIQFA (SEQ ID: 4)
and that are not homologous to and do not cross react with a nucleotide sequence of the human genome. Homologues of such sequences are also contemplated by the present invention. Because these polypeptide sequences are conserved among at least *Candida albicans, Yarrowia lipolytica, Saccharomyces cerevisiae* and *Cryptococcus neoformans* (conservation of SEQ ID: 2 has not been confirmed in *C. neoformans*) and are not known to exist in the human genome, nucleotide sequences encoding such polypeptides bind selectively and specifically to fungal nucleic acids. In a preferred embodiment, the nucleic acid hybridization probes have a sequence selected from the group consisting of:
CTTCATTTAAGAGCAGAAACTAAACCATTAGAA (SEQ ID: 14)
TTACTCGATGCTGGATTTGAA (SEQ ID: 15)
GGTTTAAAAGAATTACCTGAA (SEQ ID: 16)
CATGAACATATTCAATTTGCT (SEQ ID: 17)
TTATATGATTTAGAATTTTTAGAA (SEQ ID: 18)
GGTAGGAGAGTTGCTGCCTTTGGATTT (SEQ ID: 19)
GCTGGATTTGCTGGGGCTGCC (SEQ ID: 20)
CTTGTTATTGGTGCCTTGGGTAGATGTGGATCTGGTGCCATTGATTTA (SEQ ID: 21)
AAAGGTGGTCCATTCCAAGAAATT (SEQ ID: 22)
GATATTTTCATTAATTGTATT (SEQ ID: 23)
ATTGTTGATGTTTCTGCTGATACTACTAATCCTCATAATCCA (SEQ ID: 24)
GGTCCTAAATTATCAGTATGTTCAATTGATCATTTACCTTCTTTATTACCTAGAGAAGCTTCAGAA (SEQ ID: 25)
TTATTTGATAAACACGTTGCCAGA (SEQ ID: 26)
ATGCA GTT GAT GAA (G or A)AT (G or T)TC (SEQ ID: 27)
CAC GAG CAC ATC CAG TT(C or T) GC (SEQ ID: 28)
and the complements thereof. Fragments of the above referenced sequences are also part of the present invention as such fragments are expected to bind selectively to fungal-derived genetic material. Such sequences are homologous to the nucleic acid sequences derived from *Candida albicans* that code for the conserved polypeptide sequences set forth above and are not known to cross hybridize with sequences found in the human genome.

The invention also encompasses hybridization probes that have nucleotide sequences different from those set forth above (SEQ IDs: 14–28) if such probes code for amino acid sequences (a) derived from saccharopine dehydrogenase and (b) conserved among fungi that are not homologous to and do not cross hybridize with sequences found in the human genome.

Particularly useful embodiments of the probes may be labeled with radioactive isotopes, antigens or fluorescent compounds. Reagents comprising the inventive probes are also provided. Additionally, methods of screening a biological sample for the presence of a fungal pathogen using the above referenced probes are also provided. In such methods, hybridization may optionally be conducted on filter paper or in solution. The nucleic acid to which the probe hybridizes may be isolated from a biological sample or may remain embedded in such sample. Hybridization may be detected by techniques well known in the art, such as autoradiography. In a preferred embodiment, the probe is selected from the group of preferred hybridization probes set forth above.

In another aspect, the invention provides pairs of oligonucleotides of from about 15 to about 66 nucleotides that comprise primer pairs wherein each member of the primer pair is a nucleotide sequence selected from the group consisting of nucleic acid sequences that code for polypeptides that are (a) derived from saccharopine dehydrogenase expressed by wild type *Candida albicans* and (b) are conserved among fungi, wherein the nucleotide sequences are not homologous to and do not cross hybridize with nucleotide sequences found in the human genome and homologues thereof. In a preferred embodiment, each member of the primer pair is selected from the group consisting of nucleotide sequences coding for the following polypeptides:
LVIGALGRCGSGAIDL (SEQ ID: 8)
GPKLSVSIDHLPSLLPREASE (SEQ ID: 12)
DIFINCI (SEQ ID: 10) or
HEHIQFA (SEQ ID: 4)
and homologues thereof that are not homologous to and do not cross hybridize with nucleotide sequences contained in the human genome. In a particularly preferred embodiment, each member of a primer pair is selected from the group consisting of:
CTTGTTATTGGTGCCTTGGGTAGATGTGGATCGG-TGCCATTGATTTA (SEQ ID: 21)
GGTCCTAAATTATCAGTATGTTCAATTGATCATT-TACCTTCTTTATTACCTAGAGAAGCTTCAGAA (SEQ ID: 25)
ATGCA GTT GAT GAA (G or A)AT (G or T)TC (SEQ ID: 27)
CAC GAG CAC ATC CAG TT(C or T) GC (SEQ ID: 28)
and complements thereof. Reagents comprising primer pairs selected from the group set forth above are also provided. Methods of screening biological samples for the presence of a fungal pathogen by amplifying a nucleotide sequence using the inventive primers are also provided.

In a further aspect, the invention provides methods of using antibodies to detect a fungal pathogen in a biological sample. Such methods include detecting the binding to a biological sample of antibodies that selectively bind to epitopes of saccharopine dehydrogenase expressed by wild type *C. albicans* but that do not bind to epitopes found in human proteins. The invention additionally provides novel antibodies for use in such assays. The antibody may be labeled and the method may comprise an enzyme linked immunosorbent assay (ELISA).

In an additional embodiment, the invention provides novel fungal epitopes displayed on saccharopine dehydrogenase expressed by wild type *Candida albicans* but not displayed on mammalian proteins. These epitopes may be used to generate antibodies of the present invention. In an alternative embodiment, these epitopes may be labeled and used to detect the presence of a fungus in a biological sample, for example, by competitively inhibiting antibody binding in a radioimmunoassay. Reagents and kits comprising the inventive antibodies and epitopes are also provided.

It is an object of the invention to provide a more rapid method for testing a biological sample for the presence of a fungal pathogen than is currently available. It is a further object of the invention to provide a sensitive method of screening biological samples for the presence of a fungal pathogen, and it is a particularly important object of the invention to provide a screening method of sufficient sensitivity to identify the presence of a fungal pathogen in a biological sample taken during the early stages of infection.

Another object of the present invention is to provide a method for identifying a fungal pathogen in a biological sample that is sufficiently specific to allow clinicians to rely upon the results in deciding whether to administer antifungal therapeutic agents and in selecting the appropriate therapeutic agent. It is a further object of the present invention to provide a relatively inexpensive method for identifying fungal pathogens in a biological sample.

It is a particular object of the present invention to provide a rapid, sensitive, selective and economical method for identifying *Candida albicans* in a biological sample. Employment of such a method will allow treatment of fungal infections to begin earlier than possible with current diagnostic procedures and will therefore increase the likelihood of patient survival and shorten the duration of the fungal infection.

It is an additional object of the invention to provide nucleic acid constructs for use in screening biological samples for the presence of fungal pathogens. Another object of the invention is to provide such nucleic acid constructs that are sensitive and specific for fungal pathogens. It is a further object of the present invention to provide nucleic acid constructs for use in screening biological samples for the presence of *Candida albicans*.

An additional object of the invention is to provide antibodies for use in screening biological samples for the presence of fungal pathogens. Another object of the invention is to provide such antibodies that are sensitive and specific for fungal pathogens. It is a further object of the present invention to provide antibodies for use in screening biological samples for the presence of *Candida albicans*.

BRIEF DESCRIPTION OF THE DRAWINGS

FIG. 1 depicts schematically the enzymatic pathway known as the α-aminoadipate pathway.

FIG. 2 provides the nucleotide sequence (SEQ ID NO: 29) and amino acid sequence (SEQ ID NO:30for the LYS 1 gene of *C. albicans*.

FIG. 3 sets forth a comparison of the putative amino acid sequences for saccharopine dehydrogenase (or portions of that molecule) expressed by *C. albicans, Y. lipolytica* (SEQ ID NO:32), *S. cerevisiae* (SEQ ID NO:31) and *C. neoformans* (SEQ ID NO:33). Consensus information is provided only when a consensus exists between the sequences provided for all four organisms. Consensus among fewer than the four organisms exists in some cases, but is not indicated.

FIG. 5 sets forth a comparison of the nucleotide sequence of a portion of the LYS 1 gene of *C. albicans* (nucleotides 372–1499) and that of a portion of the *Y. lipolytica* gene for saccharopine dehydrogenase (nucleotides 663–1757).

FIG. 6 sets forth a comparison of nucleotide sequence of a portion of the LYS 1 gene of *C. albicans* (nucleotides 986–1324) with that of a portion of the LYS 5 gene from *S. cerevisiae* (nucleotides 564–919).

FIG. 7 sets forth a comparison of the putative amino acid sequence for saccharopine dehydrogenase expressed by *C. albicans* with that expressed by *Y. lipolytica*.

FIG. 8 provides the sequence of the nucleic acid fragment amplified from *Cryptococcus neoformans* genomic DNA using the probes and methods described in below in Example 6.

DETAILED DESCRIPTION OF THE INVENTION

Figure 4A:
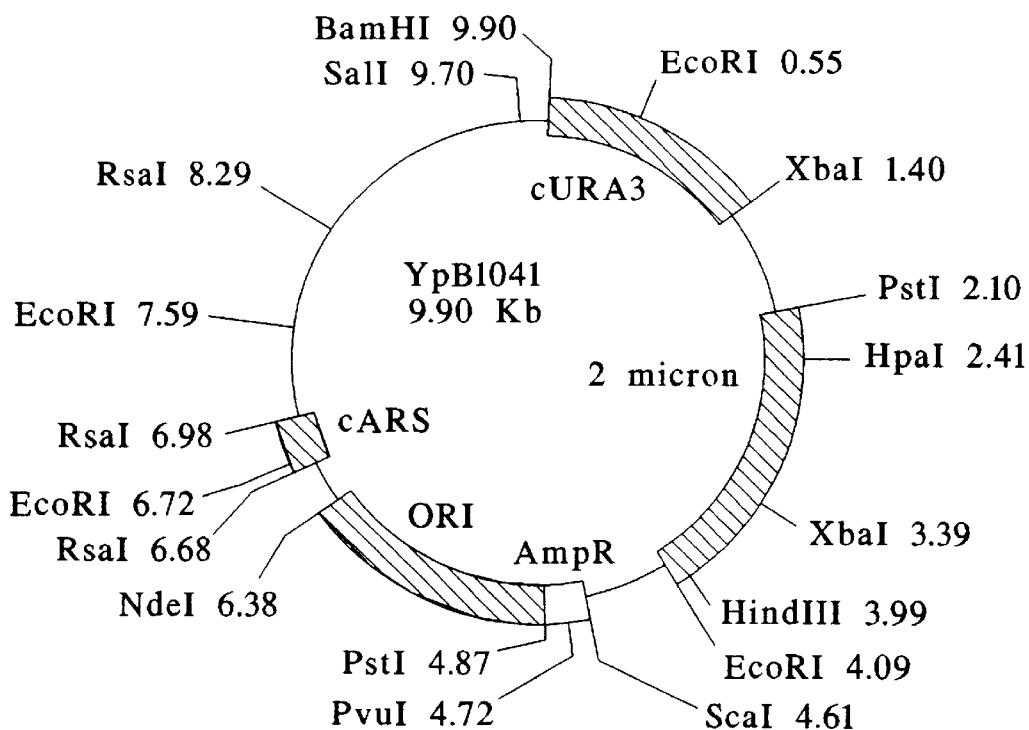
FIG. 4 depicts the vectors and plasmids used to obtain the sequence set forth in FIG. 2.

This invention provides methods and reagents for detecting fungal pathogens in biological samples. In the inventive method, the presence of a fungal pathogen may be detected using nucleic acid hybridization probes, each probe having a nucleotide sequence selected from the group consisting of nucleotide sequences that code for a polypeptide that is (a) derived from the saccharopine dehydrogenase molecule expressed by wild type *Candida albicans*, and (b) conserved among fungi, wherein such probes are not homologous to and do not cross react with nucleic acid sequences found in the human genome. Because humans do not express saccharopine dehydrogenase and the human genome is not known to contain a gene for this molecule, this molecule provides a unique starting point for generating hybridization probes that can be used to selectively detect fungal pathogens in a biological sample.

Homologues of such hybridization probes are also contemplated by the present invention. The presence of such fungal pathogens may also be detected using antibodies to such fungal specific *C. albicans* polypeptides. The inventive methods and reagents allow for the rapid and accurate identification of the infecting organism and therefore facilitate early therapeutic intervention.

Although approximately forty genes of the *C. albicans* genome have been sequenced, very few of the genes involved in amino acid biosynthesis had been sequenced prior to the current invention. The *C. albicans* LYS 1 gene codes for saccharopine dehydrogenase, one of the enzymes of the pathway used in fungi to generate lysine. This pathway is called the alpha aminoadipate pathway ("the a-AA pathway"); the enzymes and intermediates of this pathway are represented in FIG. 1. The LYS1 gene was originally cloned by Goshorn et al. (Goshorn et al. Gene isolation by complementation in *Candida albicans* and applications to physical and genetic mapping, Infect. and Imm. 60:876–884 (1992)). The sequence of the LYS 1 gene, determined by the present inventors, is set forth in FIG. 2 (SEQ ID NO: 29). The putative amino acid sequence for the LYS1 gene, also identified by the present inventors, is also set forth in FIG. 2 (SEQ ID: 30).

The present invention may be used to identify whether a subject is infected with a fungal pathogen as distinguished from a viral, bacterial or other biological pathogen. Because saccharopine dehydrogenase is not known to be expressed by bacteria or any other non-fungal organisms, it provides a unique starting point for the methods claimed herein. The invention may also be used to select appropriate antifungal drugs for use in therapeutic intervention relatively early in the disease state. It is believed that the invention is appropriate for detecting in biological samples fungal pathogens including but not limited to the following: *Candida albicans, Yarrowia lipolytica* and *Cryptococcus neoformans*. It is possible that the invention may also be appropriate for detecting *Aspergillus fumigatus* and *Histoplasma capsulatum* in a sample.

Biological samples screenable via the present invention include samples obtained from healthy subjects or those with frank or occult disease. Samples appropriate for use in the current invention should be obtained from a site on or in the body where fungi do not constitute the normal flora. The at-risk patients from which the samples are obtained include, but are not limited to mammals suffering from acquired immune deficiency syndrome, those under treatment with immunosuppressive drugs, postoperative patients and other immunocompromised patients. The samples may comprise tissues, including but not limited to swabbings from mucocutaneous membranes such as swabs from the oral cavity or the vagina, or fluids including but not limited to urine, blood, semen, cerebrospinal fluid or other bodily fluids. In a preferred embodiment, the sample is a throat swab.

The nucleic acids derived from the biological samples of the present invention may be DNA, including but not limited to cDNA, and RNA, including but not limited to mRNA. RNA derived from such samples may be particularly enriched for fungal RNAs as the fungal cells divide rapidly during infection. Thus, RNA derived from a biological sample is an important starting material for the methods of the present invention. RNA may be isolated from mixtures of DNA and RNA by using selective exonucleases, such as DNase, and other means well known in the art. Alternatively, RNA obtained from the sample can be converted to cDNA prior to employing the inventive methods.

In the present invention, nucleic acids may be isolated from the biological samples or may remain embedded in such samples. As used herein, "nucleic acids derived from a biological sample" encompasses DNAs and RNAs either isolated from or contained in a biological sample. As used herein, the phrases "polypeptide fragments derived from saccharopine dehydrogenase expressed by wild type *Candida albicans*" or "amino acid sequences derived from saccharopine dehydrogenase expressed by wild type *Candida albicans*" shall be taken to mean polypeptides having an amino acid sequence identical to any fragment of the saccharopine dehydrogenase protein derived from wild type *C. albicans*.

In methods where nucleic acids are first isolated from the biological sample prior to screening, the nucleic acid should be obtained in a manner so as to maintain it in an essentially undegraded state. It will be understood by those with skill in the art that by "essentially undegraded" is meant that the nucleic acid samples will be of sufficient integrity that the genes or messenger RNAs coding for saccharopine dehydrogenase in the sample will be detectable by the methods of this invention. Essentially undegraded nucleic acid is isolated by means well known to those with skill in the art. See, Sambrook et al., 1990, *Molecular Cloning: A Laboratory Manual* (Cold Spring Harbor Press: New York), hereby incorporated by reference. Nucleic acid samples used according to the invention may be transferred directly onto a membrane, such as a nitrocellulose or a nylon membrane, or another solid support. Conversely, isolated nucleic acids may be put into solution. Britten and David describes such methods generally and is hereby incorporated by reference.

In one particularly important aspect of the invention, the nucleic acids are not isolated from the biological sample. In such methods, hybridization probes are applied directly to a biological sample in a manner known as in situ hybridization. Biological samples appropriate for use in in situ hybridization include tissues that may optionally be sliced or embedded in a support such as wax. The tissues may also be applied to a slide. Alternatively, in situ hybridization may be conducted in vivo and hybridization determined though detection methods such as computer aided tomography. Such methods are particularly desirable as they allow for rapid processing of samples to be tested and are particularly suited to laboratory conditions or kits for clinical use.

The present inventive methods include a method for detecting a fungal pathogen in a biological sample by screening nucleic acids derived from the sample. As described above, appropriate samples include tissues, fluids, biopsies and the like.

In the inventive methods, the presence of a fungal pathogen in a sample may be detected with hybridization probes directed to nucleic acid sequences (and corresponding homologues) that code for polypeptide fragments of saccharopine dehydrogenase expressed by wild type *Candida albicans*. The hybridization probes of the present invention are not homologous to and do not cross hybridize with nucleotide sequences of the human genome. These probes may be labeled, such as with radioactive isotopes, antigens or fluorescent compounds, to allow detection and quantification of probe hybridization.

Techniques for nucleic acid hybridization are described in Nucleic Acid Hybridization, eds. Hames, B. D. and Higgens, S. J., IRL Press, Oxford (1985) which is hereby incorporated by reference. In the inventive method, nucleic acids derived from a sample (whether in single stranded or double stranded form) may be transferred to a support, such as a nitrocellulose filter or nylon membrane, or may be put into solution. If transferred to a support, the nucleic acid may be applied as a single sample or as a series of samples. Samples of double stranded DNA may then be denatured using a salt solution. The DNA may be processed prior to transfer onto the support, for example, by digesting the DNA with restriction enzymes and separating the resulting fragments on a gel.

The pattern of distribution of nucleic acid on the filter is selected based on considerations such as whether the nucleic acid bound to the filter will be hybridized with a single probe species or multiple probe species.

In one embodiment, a series of nucleic acid samples are applied to a support. These samples are bound to the support as described above. To each support, a labeled hybridization probe contained in a reagent, preferably a hybridization buffer, is applied. Such probes should be made single stranded prior to application, such as by heating briefly. The supports so treated are then incubated for approximately 6–48 hours, and washed with a moderate to high stringency wash to remove nonspecifically-hybridized probes.

The present invention contemplates the use of mixed pools of hybridization probes. Such pools would incorporate a variety of probes, such as degenerate probes or probes directed to more than one nucleotide sequence.

Hybridization is detected in a manner appropriate to the label, such as by autoradiography or fluoroscopy. Methods for detecting and quantifying hybridization are well known to those of ordinary skill in the art. In a preferred embodiment, appropriate negative (i.e. nucleic acids derived from uninfected tissue) and positive (i.e. fungal derived nucleic acids) controls are conducted to identify false negative and false positive hybridization.

Low stringency conditions are preferably employed during the annealing process to maximize hybridization of probes to homologous nucleic acid sequences. Following annealing, the filters are preferably washed under conditions of higher stringency to eliminate probes bound nonspecifically.

In one embodiment, the nucleic acid sample is screened in solution. In such a method, the isolated nucleic acid may be optionally digested such as with a restriction enzyme. Hybridization probes are added to the solution and allowed to anneal. Stringency conditions should be selected to maximize hybridization (i.e. low stringency) and then should be raised to disrupt hybridization of probes bound to non-homologous nucleicacids. Detection and quantification of hybridization may be achieved as described above.

The results of the foregoing hybridization procedures are then used to identify the presence of a fungal pathogen in the biological sample from which the nucleic acid was obtained. This information can then be used to select appropriate therapeutic agents for treatment.

In situ hybridization methods are also encompassed by the present invention. In such methods, biological samples may be applied directly to a solid support and then treated with a labeled hybridization probe. Unannealed probes are then removed, for example, by washing. Detection of hybridization may be achieved by autoradiography, fluoroscopy or visually, such as by detecting a color change.

A particularly advantageous embodiment of the present invention would be provided by a kit comprising one or more of the following elements: a solid support, a device for obtaining a biological sample from a mucocutaneous membrane (i.e. a swab), a solution containing nucleic acid hybridization probes labeled with a visually detectable label and a washing solution. Such kits may be employed, for example, by first applying the biological sample to the support, treating the sample with a solution containing the visually detectable probe, washing away the unannealed probes and visually detecting hybridization probes bound to the biological sample.

In an additional embodiment of the present invention, hybridization probes are used to detect restriction fragment length polymorphisms in nucleic acids isolated from a biological sample. In such method, nucleic acids are isolated from the sample and digested with a restriction endonuclease. The digested nucleic acids are electrophoresed and blotted, as previously described. A sample known not to contain fungal nucleic acids is used as a negative control. Labeled probes having a nucleotide sequence that codes for a polypeptide that is (a) derived from saccharopine dehydrogenase expressed by *Candida albicans*, and (b) conserved among fungi, wherein such nucleotide sequences are not homologous to and does not cross hybridize with nucleotide sequences found in the human genome, are then used to detect the presence of characteristic fragments of fungal nucleic acids in the biological sample.

The present inventive methods employ inventive reagents for the detection of a fungus in a sample. The reagents comprise inventive hybridization probes and appropriate hybridization buffers, which are known to those of skill in the art.

FIG. 3 provides a comparison of the putative amino acid sequences for the saccharopine dehydrogenase (or a fragment of this protein) expressed by wild type versions of the following organisms: *Candida albicans, Yarrowia lipolytica, Saccharomyces cerevisiae* and *Cryptococcus neoformans* (in part). These amino acid sequences provide a starting point for generating the hybridization probes and nucleic acid primers of the present invention. Areas of consensus are provided beneath the four sequences (as the amino acid sequence for the *C. neoformans* runs only from residue 89 to residue 263, no consensus information is provided for the remainder of the sequence, although conserved sequences among the remaining three organisms outside of the stretch from residue 89–263 are clear from FIG. 3). The information provided by this figure may be used to generated hybridization probes useful for detecting a fungus in a biological sample.

The degeneracy of the genetic code requires that the probes and primers that will be useful in the present invention be described in terms of the polypeptides for which they code. Evolution results in related organisms using different codons to code for identical amino acids. Thus, the probes and primers of the present invention are those described in terms of the amino acid sequences for which they code, although exemplary sequences are identified herein. For the purposes of the present invention, when a probe or a primer is identified by its sequence, such probe or primer shall be taken to include the complementary sequence.

Certain hybridization probes expected to be useful in detecting fungi in biological samples include the nucleotide sequences of the LYS 1 gene of *Candida albicans* (set forth in FIG. 2, SEQ ID NO:30) that code for amino acid sequences conserved among fungi. The amino acid sequences which are conserved between *C. albicans* and *Y. lipolytica*, and the corresponding nucleotide sequence from *C. albicans* coding for those conserved sequences are set forth in Table I;

synthesized by recombinant methods using products incorporating viral and bacterial promoters available from Promega (Madison, Wis.). The probes may be single stranded or double stranded and may comprise DNA, cDNA or RNA.

The present inventive reagents may contain hybridization probes having only a single sequence, or may contain a combination of probes homologous to a variety of nucleotide sequences. The probes may be labeled, such as with radioisotopes, fluorescent compounds or antigens, to allow their detection following hybridization. In one embodiment of the present invention, an inventive reagent contains samples of a number of different hybridization probes each sample containing a label detectable by a different method. Use of such a reagent may, for example, be used as a control

TABLE I

| CONSERVED AMINO ACID SEQUENCE | *C. albicans* LYS 1 NUCLEOTIDE SEQUENCE CODING FOR AMINO ACID SEQUENCE |
|---|---|
| LHLRAETKPLE (SEQ ID: 1) | CTTCATTTAAGAGCAGAAACTAAACCATTA GAA (SEQ ID: 14) |
| LLDAGFE (SEQ ID: 2) | TTACTCGATGCTGGATTTGAA (SEQ ID: 15) |
| GLKELPE (SEQ ID: 3) | GGTTTAAAAGAATTACCTGAA (SEQ ID: 16) |
| HEHIQFA (SEQ ID: 4) | CATGAACATATTCAATTTGCT (SEQ ID: 17) |
| LYDLEFLE (SEQ ID: 5) | TTATATGATTTAGAATTTTTAGAA (SEQ ID: 18) |
| GRRVAAFGF (SEQ ID: 6) | GGTAGGAGAGTTGCTGCCTTTGGATTT (SEQ ID: 19) |
| AGFAGAA (SEQ ID: 7) | GCTGGATTTGCTGGGGCTGCC (SEQ ID: 20) |
| LVIGALGRCGSGAIDL (SEQ ID: 8) | CTTGTTATTGGTGCCTTGGGTAGATGTGGA TCTGGTGCCATTGATTTA (SEQ ID: 21) |
| KGGPFQEI (SEQ ID: 9) | AAAGGTGGTCCATTCCAAGAAATT (SEQ ID: 22) |
| DIFINCI (SEQ ID: 10) | GATATTTTCATTAATTGTATT (SEQ ID: 23) |
| IVDVSADTTNPHNP (SEQ ID: 11) | ATTGTTGATGTTTCTGCTGATACTACTAAT CCTCATAATCCA (SEQ ID: 24) |
| GPKLSVCSIDHLPSLLPREASE (SEQ ID: 12) | GGTCCTAAATTATCAGTATGTTCAATTGAT CATTTACCTTCTTTATTACCTAGAGAAGCT TCAGAA (SEQ ID: 25) |
| LFDKHVAR (SEQ ID: 13) | TTATTTGATAAACACGTTGCCAGA (SEQ ID: 26) |

These amino acid sequences are highly conserved, with minor exceptions, among *C. albicans, S. cerevisiae* and *Yarrowia lipolytica*. As shown in FIG. 3, many of these sequences are believed to be conserved in *C. neoformans* as well, although a full amino acid sequence for the saccharopine dehydrogenase gene for *C. neoformans* has not yet been suggested or shown. Degenerate probes coding for the amino acid sequences set forth above are also contemplated by the present invention of probes coding for the foregoing amino acid sequences are obviously contemplated by the present invention.

Probes preferred for use in the present invention have a maximum length of about 400 base pairs and a minimum of about 15 base pairs. In a preferred embodiment, the probes are from about 15 to about 100 base pairs long. In an especially preferred embodiment, the probes are approximately 15–40 base pairs long. Such sequences will hybridize selectively to fungal sequences under moderately stringent conditions as provided by the methods of the invention.

The inventive probes may be made by methods well known in the art, such as chemical synthesis. They may be synthesized manually or by machine. They may also be wherein a positive result would require binding of more than one type of probe to the sample.

In addition to hybridization probes, the inventive reagents may contain components including but not limited to formamide, phosphate buffers, dextran sulphate, yeast tRNA, SDS and salt. The reagents may also comprise acetyl triammonium boride, which renders the $T_m$ of the hybridization mixture to be dependent exclusively on probe length.

The present invention also provides for the detection of fungal pathogens in biological samples following amplification of a portion of a saccharopine dehydrogenase gene, such as the LYS 1 gene. In such a method, for example, biological samples are first obtained and nucleic acids isolated as described above. Portions of genes or mRNAs coding for saccharopine dehydrogenase contained in the nucleic acid sample are then amplified by PCR (polymerase chain reaction), a technique well known to those of ordinary skill in the art. The PCR technique is described in *PCR Technology, Principles and Applications for DNA Amplification* (Erlich ed. 1989) and U.S. Pat. No. 4,683,202, the teachings of which are hereby incorporated by reference.

Inventive pairs of nucleic acid primers for use in PCR are contemplated by the present invention. Each member of such primer pair has the characteristics of the above described hybridization probes, namely, each member of the primer pair has a nucleotide sequence that is selected from the group consisting of nucleotide sequences that code for polypeptide fragments that are (a) derived from saccharopine dehydrogenase expressed by wild type *Candida albicans* and (b) conserved among fungi, wherein neither member of such primer pairs is homologous to nor cross hybridizes with nucleotide sequences found in the human genome. These inventive primer pairs, generated based on the information provided herein, including but not limited to that set forth in Table I, are employed during gene amplification.

Appropriate primer pairs are then used to amplify genetic material by well known methods. For the purposes of the present invention, a portion of a gene shall be taken to mean any portion of an entire gene, including regulatory sequences. More than one set of primer pairs may be used in the inventive method to amplify multiple gene fragments. The invention thus enables in vitro amplification of portions of fungal genes, for example, the LYS 1 gene, that can then be used in a screening procedure capable of identifying the presence of fungal pathogens in a biological sample.

It is also possible that the PCR method known as "Touchdown" PCR would be useful in the amplifying DNA from fungi when the primers to be used are degenerate. This technique is described in R. H. Don, et al., 'Touchdown' PCR to circumvent spurious priming during gene amplification. Nucleic Acids Research, 19:4008 (1991) which is hereby incorporated by reference.

The gene portions so amplified may be transferred to filters or into solution in the manner described above. Reagents containing one or more hybridization probes are then applied to the samples of the amplified nucleic acids and allowed to anneal under stringency conditions as described above. Unannealed probes are then removed by washing. Hybridization of the probes to the amplified DNA samples is then detected by means appropriate to probe label, such as by autoradiography.

The results of the hybridization experiments are then analyzed to determine the presence of a fungal pathogen in the biological sample. This information is then used in planning a course of antifungal treatment.

The primers of the present invention should be long enough to allow specific binding to fungal derived nucleic acid sequences and should have a sequence that is sufficiently homologous to a portion of the LYS1 gene to allow hybridized probes to remain bound under conditions of relatively high stringency. Each member of a primer pair to be used in connection with the present invention is selected from the group consisting of nucleic acids having nucleotide sequences coding for polypeptides that are (a) derived from saccharopine dehydrogenase that is expressed by wild type *C. albicans*, and (b) conserved among fungi, wherein the nucleic acids neither are homologous to nor cross hybridizes with nucleic acids derived from mammals. Preferably, each member of the primer pairs consist of nucleic acids having at least a portion of the nucleotide sequences set forth in Table I above. More preferably, the members of the primer pairs would have the following nucleotide sequences:

ATGCA GTT GAT GAA (G or A)AT (G or T)TC (SEQ ID: 27)

CAC GAG C(A or T)C ATC CAG TTC GC (SEQ ID: 28)

The present invention also provides methods for detecting antibody binding to epitopes contained in a biological sample. Such methods entail applying an antibody, preferably a monoclonal antibody, capable of binding selectively to an epitope of *C. albicans*-derived saccharopine dehydrogenase and detecting selective antibody binding. Such methods include immunoblotting procedures, wherein the proteins contained in a biological sample are separated by electrophoresis and transferred to a support. Preferred supports include but are not limited to nitrocellulose filters and activated paper.

Proteins can be transferred to the filter by simple diffusion, vacuum assisted solvent flow or electrophoretic elution. Antibodies (either labeled or unlabeled) are put into solution in a protein containing solvent such as BSA/PBS. The solution is then applied to the solid support harboring the blotted protein and incubated at room temperature. The blot is then washed, such as with a buffer. If the antibodies are labeled, such as with a radioactive isotope or fluorescent compound, antibody binding can then be detected. If the antibodies are unlabeled, a secondary reagent capable of disclosing bound antibody, such as avidin or streptavidin is then added. Such secondary reagents may be enzyme labeled secondary reagents, such as those commonly utilized in enzyme linked immunosorbent assays.

The inventive antibodies may also be used to detect a fungal pathogen in a sample by means of immunoprecipitation, such as an Odin single diffusion or Ouchterlony double diffusion test. Optionally, the proteins of the sample may be separated prior to exposure to the inventive antibodies. In an alternative embodiment, the sample may first be immunoprecipitated and subsequently separated by gel electrophoresis.

Antibodies capable of binding selectively to epitopes of *Candida albicans*-derived saccharopine dehydrogenase are particularly desirable for use in detecting the presence of a fungus in a biological sample as such epitopes are not known to have counterparts among human proteins.

Antibodies, including but not limited to monoclonal antibodies, capable of selectively binding to saccharopine dehydrogenase in a biological sample can be generated through the use of hybridoma technology and related technologies well known in the art. Generation of monoclonal antibodies is described in Antibodies: A Laboratory Manual, eds. Harlow and Lane, Cold Spring Harbor, 1988, which is hereby incorporated by reference. The region of binding of such antibodies may be determined by first subjecting the target protein to enzymatic or chemical degradation, separating the fragments using electrophoresis and then immunoblotting.

In a particularly advantageous embodiment of the present invention, the inventive antibodies are employed in an enzyme linked immunosorbent assay (ELISA). In such method, the inventive antibody (the primary antibody) is anchored to a support, such as a multi-well microtiter plate. A biological sample is then added to the support, after which unbound sample is removed by washing. A second antibody to which an enzyme has been linked is applied to the support. The second antibody is one that is capable of binding to a fungal protein, though not necessarily specifically. The linked enzyme is one capable of producing a change, such as a color change, in a solution containing its substrate, the rate of color change being proportional to the enzyme concentration.

After removal of the unbound secondary antibody, a solution of the enzyme substrate is added to the support and the rate of change, such as color change, of the solution is measured. Use of such a method allows for the detection and quantification of epitopes in the sample to which the primary inventive antibody selectively binds.

In an additional aspect, the inventive methods provide a sandwich binding assay. In such an assay, the biological sample is first applied to a support, such as a filter. A inventive antibody (a primary antibody) is then applied to the support, such as by diffusion. After unbound primary antibody is removed by washing, a second labeled antibody is applied to the support. This second labeled antibody is capable of binding to the primary antibody. Appropriate labels include but are not limited to radioactive isotopes, colored compounds and fluorescent compounds.

Unbound secondary antibody is then removed by washing. Detection of a fungal pathogen in the sample is then achieved by measuring the presence of the antibody label on the support visually, or by methods such as autoradiography or fluoroscopy.

The invention also provides novel epitopes comprising polypeptides having amino acid sequences characteristic of fungi. Such epitopes may be synthesized by methods well known in the art. Such methods include both manual and automated methods of polypeptide synthesis that may be conducted in solid phase or in solution.

In a further embodiment, the invention provides a method of detecting fungal pathogens in a biological sample by means of a radioimmunoassay (RIA). In such a method, a sample of radioactively labeled inventive epitopes of known concentration are combined with a sample of inventive antibodies, also of known concentration. The amount of unbound epitope contained in the solution is then measured (the first measurement). To a solution containing a known concentration of radioactively labeled inventive epitope and unlabeled inventive antibody is then added a biological sample suspected of harboring a fungus. The amount of unbound labeled epitope in the solution is then measured (the second measurement). The first measurement is then compared to the second measurement to detect the amount of labeled epitope displaced by epitope contained in the biological sample. These results can then be used to quantify the amount of epitope contained in the biological sample. Use of a radioimmunoassay to detect fungal pathogens in a biological sample is especially desirable as it is a particularly sensitive assay.

The invention is illustrated by the following examples.

EXAMPLE 1

The LYS1 gene of *Candida albicans* codes for saccharopine hydrogenate

Figure 4B:
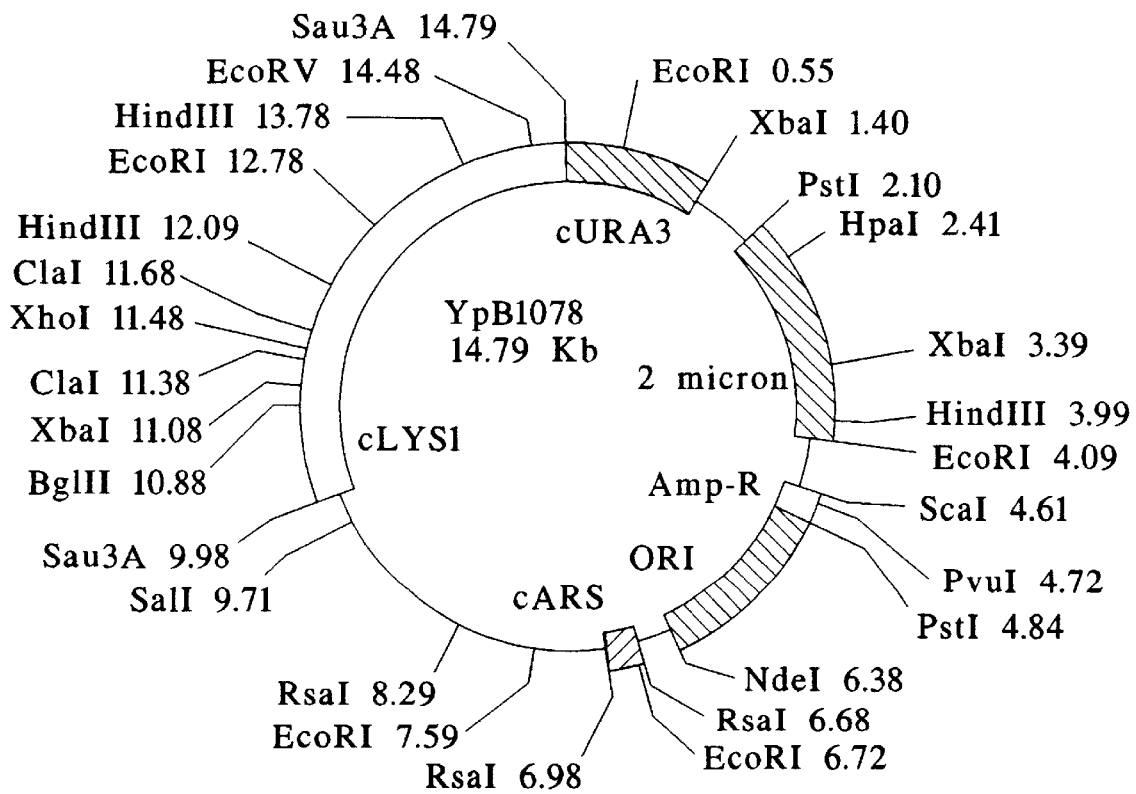
Figure 4C:
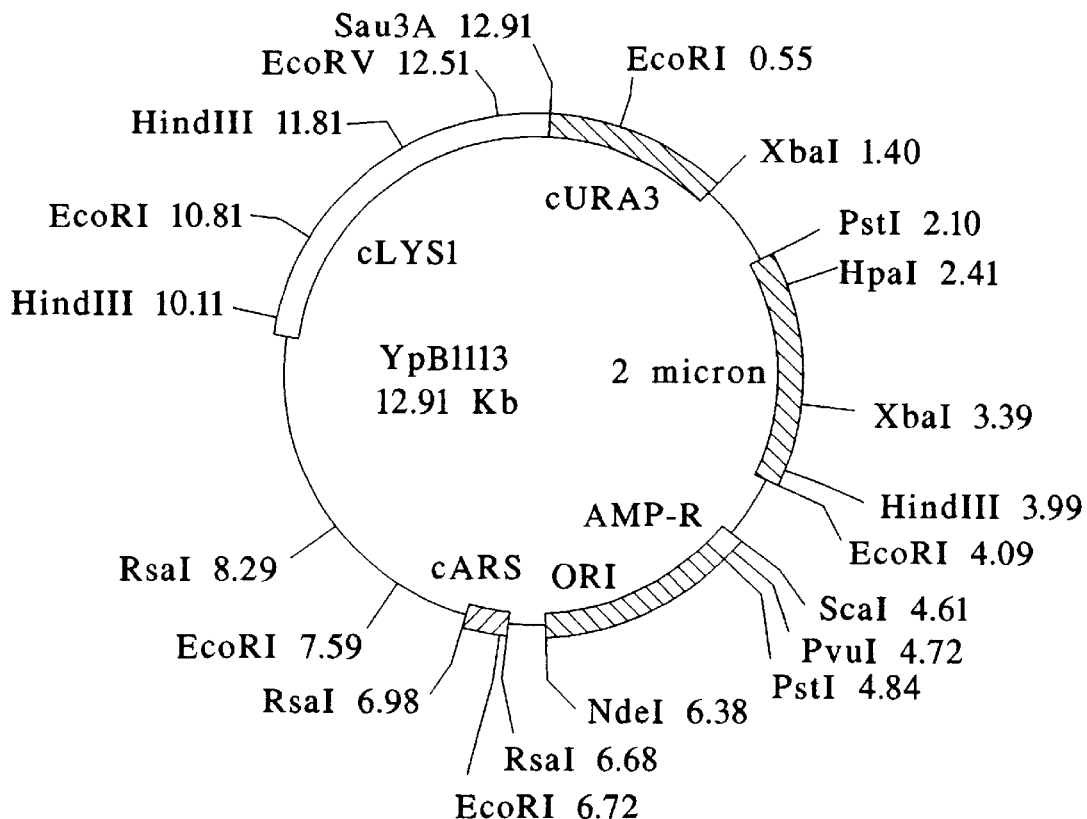
Figure 4D:
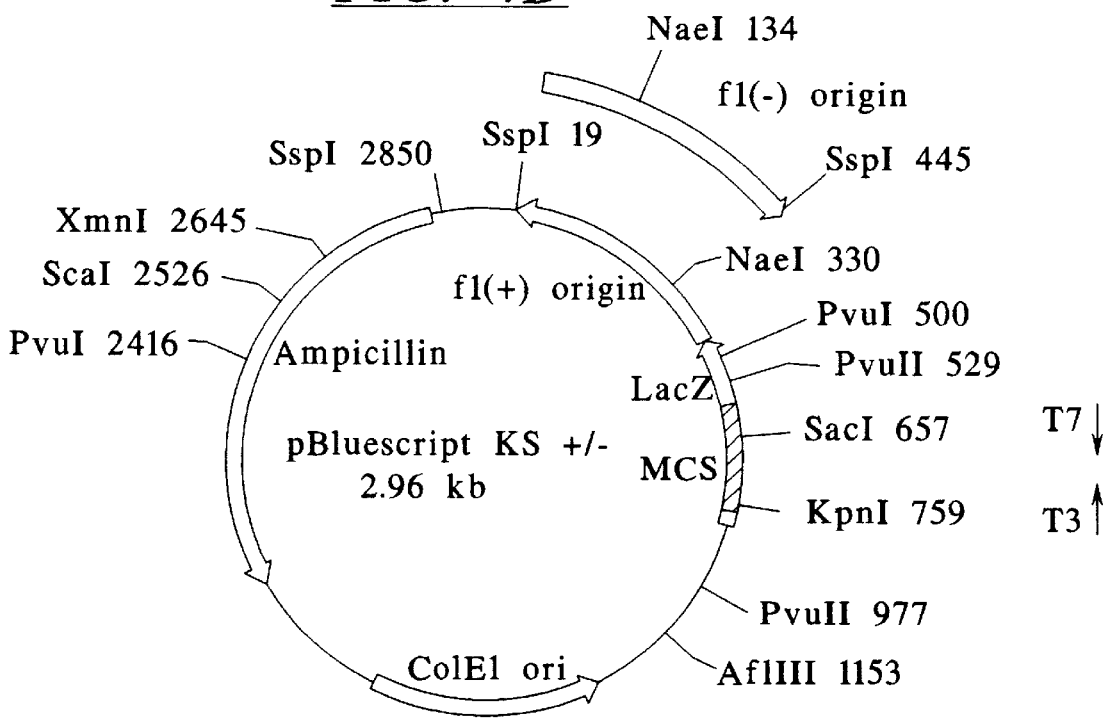
Figure 4E:
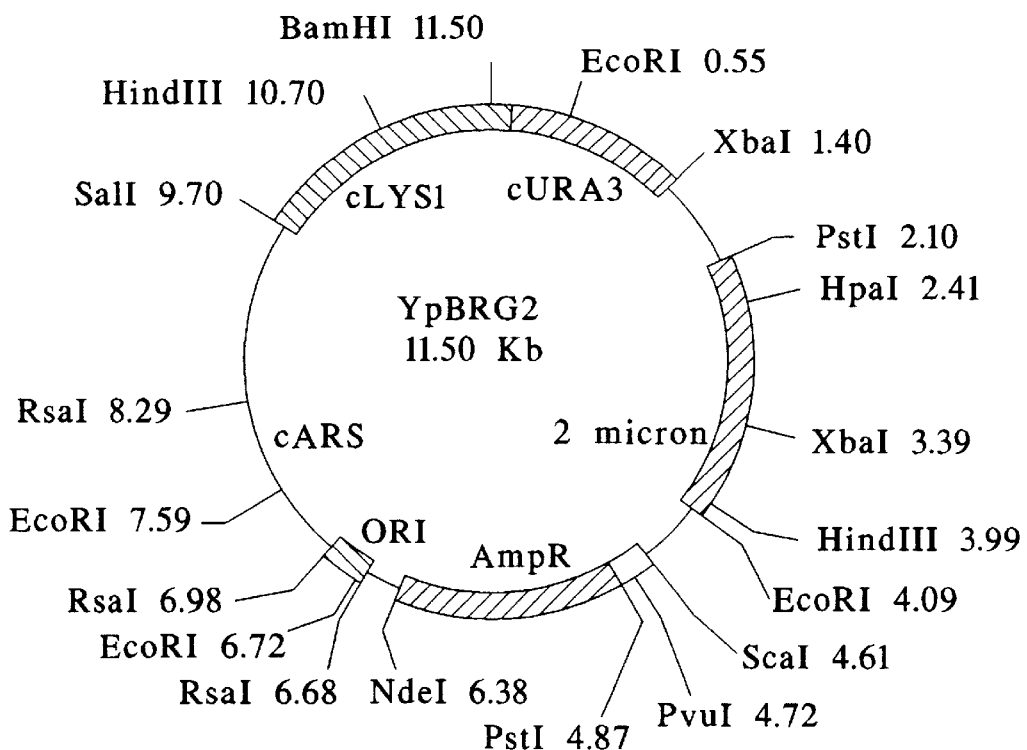
Figure 4F:
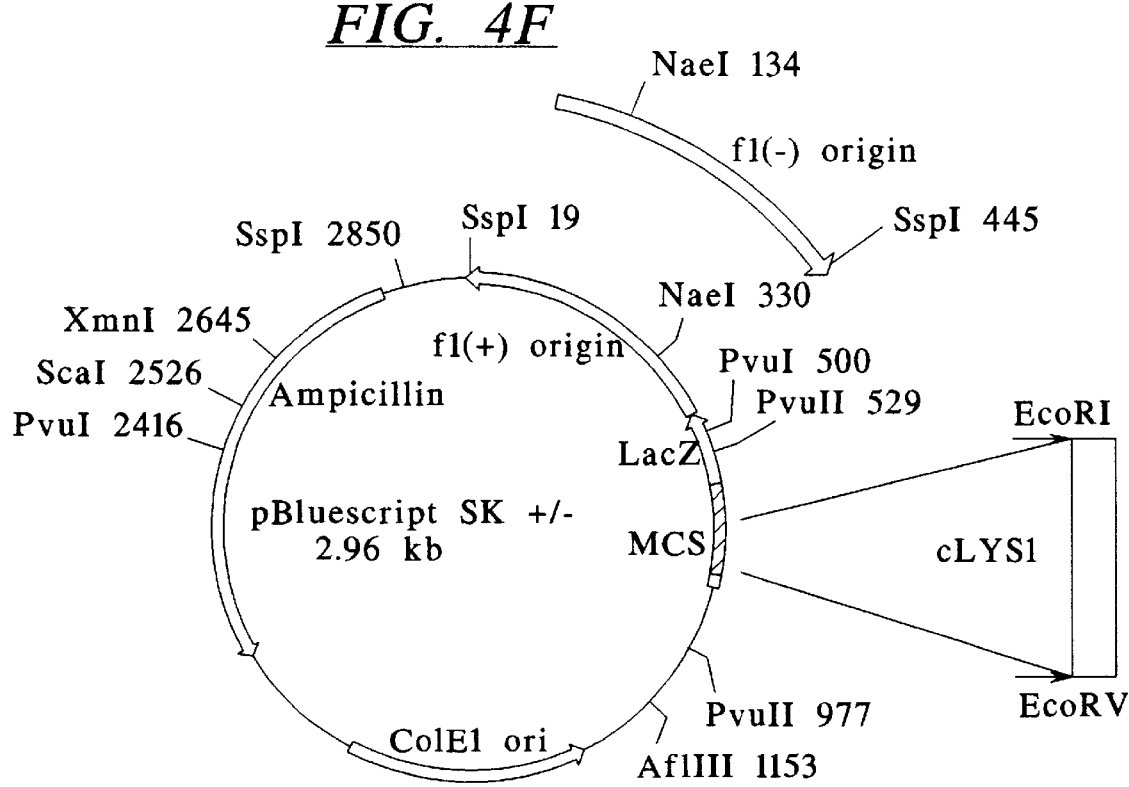

A shuttle vector, ypB1041 was first constructed by Goshorn et al. (1992). The vector is a high copy number plasmid in *S. cerevisiae*, *C. albicans* and *E. coli*. The plasmid contains the 2 μm circle for replication in *S. cerevisiae*, an ARS sequence from *C. albicans* and the pBR322 origin of replication for maintenance in *E. coli*. The plasmid may be selected for in *E. coli* by resistance to ampicillin and in yeast by the presence of the URA3 sequence. This vector and constructs YpB1078 and YpB1113 were obtained from Dr. S. Scherer (Univ. of Minnesota). The vector YpB1041 is shown in FIG. 4.

A *C. albicans* genomic library was created by Goshorn et al. by first partially digesting *C. albicans* DNA with Sau3Al. Fragments of 5 to 10 kb were gel purified and ligated into BamH1 restricted and alkaline phosphatase treated YpB1041. A single resulting clone, YpB1078, was confirmed to be capable of transforming a lysine auxotroph of *S. cerevisiae* and *C. albicans* to heterotrophy (Goshorn et al. Gene isolation by complementation in *Candida albicans* and applications to physical and genetic mapping, Infect. and Imm. 60:876–884 (1992)). The plasmid was designated YpB1078 and was the original LYS1 clone.

The first subclone of LYS1, YpB1113, was created by cutting YpB1078 with Sal1 and Cla1, gel purifying the large fragment, filling in the ends with T4 DNA polymerase and deoxynucleoside triphosphates and performing a ligation of the segment. The ability of this plasmid to transform *C. albicans* lysine auxotrophs was demonstrated as described above and is described in more detail in Goshorn et al., 1992.

A second subclone, YpBRG2 was constructed by the present inventors by cutting YpB1113 with EcoR1 and EcoRV. The sequencing and characterization of the LYS 1 gene is described in the dissertation of Richard C. Garrad entitled "The Molecular and Functional Analysis of the LYS 1 gene of *Candida albicans* And Characterization of Lysine Auxotrophs of Candida Spp." completed in partial fulfillment of the requirements for Dr. Garrad's degree of Doctor of Philosophy conferred by Miami University of Ohio, the disclosure of which is hereby incorporated by reference. This topic has also been addressed in R. Garrad et al., Molecular and Functional Analysis of the LYS1 Gene of *Candida albicans*, Infection and Immunity, 62:11 5027–5031 (1994), the disclosure of which is also hereby incorporated by reference. The subsequent 1.8 kb band was removed as a gel slice and the DNA was then electroeluted using an LUTRAP™ system (Schleicher and Schuell, Keene, N.H.) or by the method described later in this section. A similar procedure was performed on pBluescript SK. The DNAs were recovered using the method described in this section. The 1.8 kb fragment and the EcoR1/EcoRV digested PBLUESCRIPT SK were ligated for 2 hours at room temperature. The ligation mix consisted of 79 μL of sterile distilled water, 10 μL 10× ligase buffer (500 mM Tris-HCl, 10 mM MgCl2 and 10 mM ATP), 10 μL 50% PEG, 1 μL 100 mM dTT and 5 U T4 DNA ligase. The 1.8 kb fragment was thereby ligated into the multiple cloning site of pBSSK(±) (Stratagene Cloning Systems, La Jolla Calif.).

pBSSK(±) is a phagemid derived from pUC19 and marketed by Stratagene Cloning Systems, La Jolla Calif. The vector possesses an f1 phage origin, a ColE1 origin and T3 and T7 promoters flanking a multiple cloning site (MCS) containing 23 unique restriction sites. The vector contains a lacZ promoter for blue/white color selection. Primer sequences flank the MCS to facilitate DNA sequencing using the method of Sanger et al. (1977). The vector is shown in FIG. 4.

The fragment was removed from pBSSK by cutting with BamH1 and Sal1 and ligating into a similarly cut YpB1041 using the gel purification, electroelution and ligation procedures described later. The plasmid was designated YpBRG2 and is shown in FIG. 4.

EXAMPLE 2

The ability of YpB1078 (FIG. 4), YpB1113 (FIG. 4) and YpBRG2 to transform *S. cerevisiae* Stx4-4A, (Yeast Genetics Stock Center, University of California, Berkely) was demonstrated. The ability of YpBRG2 to complement saccharopine dehydrogenase mutants of *S. cerevisiae* is shown in the Table below. The Table shows transformation of various Saccharomyces strains with the LYS 1 gene from *C. albicans*. Those strains deficient in saccharopine dehydrogenase were transformed to prototrophy with a plasmid carrying the LYS 1 gene. The amount of background, indicated by the number of colonies from cells receiving no DNA and plasmid YpB1041 is constant. Although this background is higher than ideal it is consistently at this level. *S. cerevisiae* STX4-4A is a point mutant and has a reversion frequency of <7 per $10^9$ cells per mL of culture.

TABLE

Sarccharopine dehydrogenase activity of wild type, lys1 mutants and Lys1+ transformed strains of S. cerevisiae.

| Organism and Strain | Lysine Genotype | Saccharopine dehydrogenase activity[a] |
|---|---|---|
| S. cerevisiae | | |
| WT | LYS1 | 0.49 (±0.01) |
| STX4-4A | lys1 | 0.08 (±0.01) |
| STX4-4A-8 (YpB 1078)[b] | Lys1+ | 0.26 (±0.05) |
| STX4-4A-8 (YpB 1078)[c] | lys1 | 0.06 (±0.01) |
| STX4-4A-3 (YpB RG2)[b] | Lys1+ | 0.89 (±0.22) |
| STX4-4A-3 (YpB RG2)[c] | lys1 | 0.09 (±0.01) |
| STX4-4A-4 (YpB RG2)[b] | Lys1+ | 0.69 (±0.22) |
| STX4-4A-4 (YpB RG2)[c] | lys1 | 0.14 (±0.01) |
| STX4-4A-5 (YpB RG2)[b] | Lys1+ | 0.74 (±0.19) |
| STX4-4A-5 (YpB R02)[c] | lys1 | 0.13 (±0.01) |

[a]Saccharopine dehydrogenase specific activity expressed as change in absorbance at 340 nm per min. per mg. protein.

EXAMPLE 3
Preparation of Double Stranded Template for DNA Sequencing

Double stranded templates were subjected to alkaline denaturation prior to annealing with an oligonucleotide primer. The template DNA (4 μg) was diluted to 18 μL with sterile distilled water. This solution was treated with 2.0 μL of freshly made 0.2 NaOH in 0.2 mM EDTA. The mixture was incubated at room temperature for 5 minutes and then neutralized with 8.0 μL of 5M ammonium acetate (pH 7.5). The DNA was precipitated by addition of 60 μL of 95% ethanol followed by incubation at −70° C. for at least 15 minutes. The DNA was pelleted by centrifugation at 10,000×g for 10 minutes. The pellet was dried under vacuum at 45° C. for 1 hour. The dried pellet was then resuspended in 7 μL of sterile distilled water.

Preparation of single stranded DNA

Alternatively, single stranded DNA was produced to optimize the number of bases able to be read during DNA sequencing. Single stranded DNA can be produced if the sequence of interest is cloned into a suitable vector, in this case PBluescriptSK ± and the plasmid is present in an E. coli strain which carries an F factor. Bluescript SK is a phagemid derived from pUC19 which contains f1 filamentous phage origins of replication allowing recovery of a strand of the vector when the host strain is co-infected with a helper phage. The helper phage used in this procedure was M13KO7.

The M13KO7 must be grown from fresh plaques. The stock phage was first inoculated onto a B agar plate prepared with 1 g tryptone, 0.8 g NaCl per 100 mL of sterile distilled water sterilized by autoclaving, plus 1 mL of filter sterilized 20% glucose plus 0.6 g agar per 100 mL. A 0.5 mL volume of mid-log phase E. coli NM522 (1 mL of overnight cells in 10 mL of LB broth incubated at 37° C. for 1 hour in a shaker incubator) was added to 4 mL of B top agar, mixed and poured across the phage inoculated B agar plate. The plates were incubated for 8–12 hours at 37° C. The resulting plaques were scraped from the plates and used to inoculate 100 mL of LB broth containing 70 μg/mL of kanamycin. The broth was incubated for 10–14 hours at 37° C. The cells were pelleted and the supernatant used for phage titering. This stock will remain viable for more than a year if stored at 4° C.

The phage was titered as follows: 100 μL of phage stock was diluted in 9.9 mL of B broth (1 g tryptone, 0.8 g NaCl per 100 mL of sterile distilled water, sterilized by autoclaving, plus 1 mL of filter sterilized 20% glucose). The serial dilution was repeated 5 times and from the last two dilution tubes 100 μL was taken and added to 200 μL of log phase E. coli NM522. The phage/E. coli mixture was allowed to remain at room temperature for 5 minutes. Following this brief incubation, 4 mL of B top agar at 45° C. was added to the preparation and the entire mixture poured onto a B plate. These plates were incubated at 37° C. overnight. The number of plaques were counted the next day and the titer of the phage calculated.

To produce single stranded DNA the cells harboring the pBluescript vector plus the fragment of interest were grown overnight at 37° C. in LBA broth with continual shaking. A 50 mL LBA broth culture in a 250 mL flask was inoculated with 1 mL of this overnight culture and incubated at 37° C. for 30 minutes. Helper phage M13KO7 was added to the culture at a multiplicity of infection of 20 (e.g. 200 μL of phage at a titer of $1\times10^{11}$ PFU/mL). Incubation was continued for 30 minutes and then 70 μL of kanamycin (50 mg/mL) was added and incubation continued for 10–14 hours. The culture was transferred to a 50 mL Oak Ridge tube and centrifuged to remove the cells at 17,000 g for 15 minutes in a Sorvall RC5 centrifuge. The supernatant was promptly removed and recentrifuged. The volume of supernatant was then determined and for each mL of fluid 0.25 mL of a 3.5M ammonium acetate/20% PEG 6000 solution was added, the tube was inverted to mix and then incubated on ice for 30 minutes. The mixture was centrifuged at 17,000×g for 15 minutes. The supernatant was removed and the pellet resuspended in approximately 200 μL of TE buffer (10 mM Tris.HCl pH 8.0 and 1 mM $Na_2EDTA$) and placed in a microfuge tube. An equal volume of equilibrated phenol/chloroform was added to the DNA, the solution was vortexed for 1 minute and then spun in a microfuge at full speed for 5 minutes. The top aqueous phase was removed and transferred to another microfuge tube. This procedure was repeated a number of times until the interface between aqueous and nonaqueous phases was clear. An equal volume of chloroform was added to the suspension and the mixture centrifuged. The supernatant was removed into another tube and the DNA was precipitated by the addition of 100 μL 7.5M ammonium acetate and 600 μL of 95% ethanol. The tube was incubated at 70° C. for at least 30 minutes. The tube was centrifuged for 15 minutes at 4° C. followed by removal of supernatant and drying of the pellet in the Speedvac. The DNA was finally resuspended in 20 μL of TE buffer. Typical yields of single stranded DNA were approximately 50 μg.

EXAMPLE 4

DNA sequencing of the LYS1 gene was performed using the methods described in the product guide of the SEQUENASE Version 2.0 kit (United States Biochemical, Cleveland, Ohio). The Sequenase kit employs a modification of the dideoxy chain termination method originally described by Sanger et al (1977). The DNA polymerase used in the kit is bacteriophage T7 DNA polymerase genetically engineered to remove all 3'–5' exonuclease activity.

Double and single stranded DNA templates were prepared as described above. DNA oligonucleotide primers were prepared by technical staff at Miami University on the MILLIGEN 7500 DNA synthesizer, or at the DNA core facility of the University of Cincinnati. The oligonucleotide primers used for DNA sequencing in this study are shown in Table 2. Prior to synthesis all oligonucleotides were analyzed for self hybridization and secondary structures using the Patterns and Loops subroutine of the DNA Star software program. The concentrations of the template DNA and oligonucleotide primers were determined from the values obtained using a GILFORD UV/Visible spectrophotometer set at 260 nm absorbance. A molar ratio of 1.5/1.0 (primer/template) was used in each sequencing reaction.

TABLE 2

Oligonucleotide primers used in the sequencing of the C. albicans LYS1 gene.

| NAME | SEQ ID NO # | SEQUENCE (5'--3')[a] |
| --- | --- | --- |
| Rev2RGBS2 | 1 | CACAGATACTAATTAAG |
| RBSRG2EXT2 | 2 | CTGAAGCTTCTCTAGG |
| BSRG2EXT2 | 3 | CCTAGAGAAGCTTCAG |
| RRGBS2 | 4 | GAAAATATCCAGATCCAAC |
| RGBS2EXT | 5 | GTTGATCTGGATATTTTC |
| RevCAN1LYS1 | 6 | GACTCCATATCCTAATG |
| CAN3LYS1 | 7 | CTTGCCAACCAGCTTGATC |
| RevCAN3LYS1 | 8 | GATCAAGCTGGTTGGCAAG |
| NRevCAN3LYS1 | 9 | GTACCTGAAGGTTCATG |
| CAN5LYS1 | 10 | GCAGCTCTAGCTTCTAATGG |
| RevCAN5LYSI | 11 | CCATTAGAAGCTAGAGCTGC |
| CAN7LYS1 | 12 | GATAATTCCGTCTAAAGT |
| RevCAN7LYS1 | 13 | GACGGAATTATCTCTGTCTC |
| RevCAN9LYS1 | 14 | GTGTGCACGTCCAACTC |
| SP2 | 15 | AACAGCTATGACCATG |
| SP1 | 16 | GTAAAACGACGGCCAGT |

[a]The primers were designed from pBluescript sequences or from sequences of yeast DNA during the dideoxy sequencing procedure.

Annealing template and primer. Prepared double stranded template and single stranded template were treated in a similar fashion except 4 µg of the former template was resuspended in 7 µL of sterile distilled water. To the 7 µL of prepared template, 1 µL of oligonucleotide primer and 2 µL of 5× reaction buffer (200 mM Tris.HCl pH 7.5, 100 mM $MgCl_2$ and 250 mM NaCl) were added and the mixture incubated at 65° C. for 2 minutes. This sample was allowed to cool to room temperature over a period of 30 minutes. During this time the 5× labeling mix (7.5 µM dGTP, 7.5 µM dCTP, 7.5 µM dTTP) was diluted five fold in sterile distilled water. Four microcentrifuge tubes with 2.5 µL of each of the termination mixes, ddG (80 µM dGTP, 80 µM dATP, 80 µM dTTP, 80 µM dCTP, 50 µM NaCl and 8.0 µM ddGTP), ddA (80 µM dGTP, 80 µM dATP, 80 µM dTTP, 80 µM dCTP, 50 µM NaCl and 8.0 µM ddATP), ddC (80 µM dGTP, 80 µM dATP, 80 µM dTTP, 80 µM dCTP, 50 µM NaCl and 8.0 µM ddCTP) and ddT (80 µM dGTP, 80 µM dATP, 80 µM dTTP, 80 µM dCTP, 50 µM NaCl and 8.0 µM ddTTP) were prepared.

Labeling reaction. Once the template/primer mix was annealed 1 µL of DTT (0.1M), 2 µL of diluted labeling mix, 0.5 µL of [$\alpha$-$^{35}$S] dATP (12.5 uCi/µL) and 2 µL of previously diluted Sequenase Version 2.0 enzyme (1/8 in Enzyme Dilution Buffer-10 mM Tris.HCl pH 7.5, 5 mM DTT and 0.5 mg/mL BSA) were added. The mixture was allowed to incubate at room temperature for 5 minutes.

Termination reactions. The termination mixes were incubated for at least 1 minute at 37° C. prior to addition of 3.5 µL of the completed labeling mix. The contents of each tube were mixed and incubated at 37° C. for 5 minutes. After incubation 4 µL of stop buffer (95% formamide, 20 mM EDTA, 0.05% bromophenol blue and 0.05% xylene cyanol) was added to each tube. These reactions could be stored at 20° C. without degradation. The termination reactions were heated to 75–80° C. for at least 2 minutes before loading the sequencing gel.

Denaturing Sequencing Gel Electrophoresis. All sequencing gels were 38.5 cm×31 cm×0.4 mm and were electrophoresed using a BRL model S2 sequencing gel apparatus. The two glass plates which constituted the gel mold were cleaned thoroughly with detergent followed by sterile distilled water and then ethanol. Once the plates were dry a layer of Sigmacote (Sigma Laboratories, St. Louis, Mo.) was applied to the larger of the plates to enable easy removal after electrophoresis. Finally the large plate was given a final rinse with sterile distilled water. The two plates were placed together and separated by 0.4 mm Teflon or Kevlar spacers and the resulting gel sandwich was held together by insulating tape.

The gels were prepared from a 40% stock acrylamide solution containing 190 g acrylamide and 20 g bisacrylamide (38%:2% w/v) in a final volume of 500 mL of sterile distilled water. A stock solution of 10× Tris-Borate EDTA (TBE) running buffer was prepared by dissolving 121.1 g Tris-base, 55 g boric acid and 7.4 g EDTA $Na_2.2H_2O$ in 1 liter of sterile distilled water to give a final pH of 8.3. The stock TBE was diluted to 1× when used to prepare gels and as an electrophoresis running buffer.

The preparation of 6% or 8% acrylamide gels required 15 mL or 20 mL of 40% stock acrylamide solution. In addition 50 g of urea (Fisher Scientific electrophoresis grade) and 10 mL of 10× TBE buffer were mixed until the urea was completely dissolved. The volume was made up to 99 mL with sterile distilled water. Finally the acrylamide was polymerized by the addition of 1 mL of freshly prepared 10% ammonium persulfate and 20 µL of TEMED. The solution was dispensed into the gel mold and air bubbles were removed by gentle tapping of the glass plates prior to polymerization of the solution. The flat edges of two sharkstooth combs were inserted side by side to a depth of approximately 3 mm between the two glass plates at the top of the gel mold.

Once polymerization was complete, the combs were removed, the tape was taken off the gel and the mold placed in the sequencing apparatus. The combs were washed and dried and placed back into the mold in the same position except now with the tips of the comb touching the acrylamide surface. The top and bottom chambers of the electrophoresis system were filled with an adequate amount of TBE running buffer (500 mL in each chamber). A needle and syringe were used to flush the formed wells of debris. A pre-electrophoresis run was performed. Several wells were loaded with 2 µL of stop solution and the gel was run for 15–20 minutes at 1800V and 45 mA. The gel was run for the desired time with the wells loaded with samples for sequence analysis.

After electrophoresis, the gel plates were dismantled and the gel (now stuck to the small plate) was carefully lowered into a solution of 10% acetic acid/12% methanol and left to soak for at least 30 minutes. Following this period the plate was removed from the acetic acid/methanol solution. Two pieces of Whatman 3MM filter paper of larger size than the gel were placed over the gel. The larger glass plate was then placed on top of the filter papers to create a sandwich. After about 5 minutes, the filter paper, to which the gel was adhering, was lifted from the small glass plate. The gel was dried with heat in a HOEFER gel dryer (approximately 90 minutes) under vacuum created by a SAVANT GP100 vacuum pump. The dried gel was exposed to Kodak XA5 film for 24 hours at room temperature. Films were developed in Kodak D-19 for 5 minutes followed by a 1 minute wash in water and 5 minutes in Kodak dryer. The autoradiographs were rinsed in tap water for approximately 30 minutes, dried and analyzed.

Generation of a nested set of deletions using Exonuclease III digestion. The relatively large size (1.8 kb) of the insert of interest in pBluescriptSK cLYS1 makes the creation of a set of nested deletions an attractive alternative to "walking" along the insert with overlapping primers. Exonuclease III will specifically digest DNA away from a 5' protruding or blunt end restriction site. Exonuclease III will perform this digestion in a time dependent manner, however, the sequencing primer site in the vector must be protected from digestion by the generation of a 3' overhang or by an α-phosphothioate filled end. The method used in this project made use of the ERASE-A-BASE System (Promega) based on the procedure developed by Henikoff (1984, 1987).

The 1.8kb insert containing the LYS1 gene was cloned into pBluescript at the multiple cloning site. This construction allowed digestion from each side of the insert, using BamHI (Exonuclease III sensitive) and SacI (Exonuclease III resistant) from one side and ClaI (Exonuclease III sensitive) and KpnI (Exonuclease III resistant) from the other side. After digestion with one of the pairs of restriction enzymes the reaction was checked for complete digestion by agarose gel electrophoresis. If digestion was judged to be complete the mixture was extracted with 1 volume of TE saturated phenol/chloroform. The suspension was vortexed for 1 minute and centrifuged at 12,000×g for 5 minutes. The upper aqueous phase was removed to a fresh tube and 1 volume of chloroform/isoamylalcohol (24/1) was added, the mixture was then vortexed for 1 minute and centrifuged as before. The upper phase was transferred to a fresh tube and 1 volume of 2M NaCl plus 2 volumes of 95% ethanol were added. The suspension was mixed by inverting the tube several times and the tube was incubated at 70° C. for at least 30 minutes. The tube was centrifuged at 12,000×g for 10 minutes and the pellet was dried under vacuum.

The DNA pellet was dissolved in 60 μL of Exonuclease III 1× buffer (10× buffer contains 660 mM Tris.HCl pH 8.0 and 6.6 mM $MgCl_2$). While the DNA was being resuspended 7.5 μL of S1 nuclease mix was added to each of 24 microfuge tubes and kept on ice. The S1 nuclease mix was made previously (enough for 25 tubes) by adding 60 U of S1 nuclease to 27 μL of S1 7.4× buffer (0.3M potassium acetate pH 4.6, 2.5M NaCl, 10 mM $ZnSO_4$ and 50% glycerol) plus 172 μL of sterile distilled water. The DNA was pre-warmed to 37° C. and 300–500 U of Exonuclease III was added with subsequent rapid mixing. At 30 second intervals 2.5 μL samples were removed from the DNA/Exonuclease III tube and placed in the S1 nuclease mix. Once all the samples had been taken the tubes were removed from ice and placed at room temperature for 30 minutes. Following this incubation period 1 μL of S1 stop buffer (0.3M Tris base and 0.05M EDTA) was added to the tubes and the samples were heated at 70° C. for 10 minutes to inactivate the S1 nuclease. The extent of digestions was determined by removing 2 μL samples from each time point and analyzing by agarose gel electrophoresis. The samples from each time point were transferred to 37° C. and 1 μL of Klenow mix, containing 30 μL of Klenow buffer (20 mM Tris.HCl pH 8.0 and 100 mM $MgCl_2$) and 3–5 U Klenow DNA polymerase, was added to each tube. The samples were incubated for 3 minutes and then 1 μL of dNTP mix (0.125M each of dATP, dCTP, dGTP and dTTP) was added followed by a further 5 minutes incubation. The samples were ligated. The tubes were transferred to room temperature and 40 μL of ligase mix was added to each mixture. The ligase mix contained 790 μL sterile distilled water, 100 μL ligase 10× buffer (500 mM Tris.HCl pH 7.6, 100 mM $MgCl_2$ and 10 mM ATP), 100 μL 50% PEG, 10 μL 100 mM DTT and 5 U T4 DNA ligase. The tubes were mixed well and incubated at room temperature for 1 hour. Following the ligation this mixture was used directly for the transformation of competent E. coli DH5α. Plasmids from E. coli DH5α transformants were prepared by mini-preparations, cut with an unique restriction enzyme and analyzed using agarose gel electrophoresis to distinguish clones of useful sizes. Plasmids of the necessary size were prepared by large scale preparation for subsequent DNA sequence analysis.

Analysis of DNA sequence data. The DNA sequence and protein data were analyzed using various programs available with the Genetics Computer Group software developed at the University of Wisconsin. The sequence so derived is set forth in FIG. 2.

EXAMPLE 5

Base pairs 372–1499 of the nucleotide sequence obtained in Example 3 was compared to base pairs 663–1757 for the saccharopine dehydrogenase gene of Yarrowia lipolytica (this gene is named LYS5, the sequence for which was published by Xuan et al. (1990)). The comparison is set forth in FIG. 5. For the portions of the two genes compared, the homology is approximately 61%. A comparison of base pairs identified 1–329 (identified as bases 986–1315 in FIG. 2) of the LYS 1 of C. albicans gene to base pairs 564–919 of the gene for saccharopine dehydrogenase derived from Saccharomyces cerevisiae is set forth in FIG. 6. The homology between these two gene fragments is approximately 67%.

The nucleotide sequences described above do not appear to have significant homologs in any human gene based on a Genebank search. Thus, these regions of the LYS1 and LYS5 genes are particularly useful as starting points for constructing hybridization probes for the detection of fungal pathogens, including but not limited to C. albicans, in a biological sample.

The nucleotide sequencing data was also used to determine the putative amino acid sequence of the LYS1 gene. This sequence was compared to the predicted amino acid sequence of the LYS5 gene (Xuan et al.). This comparison is set forth in FIG. 7. The sequence of the LYS 1 gene is set forth above that for the LYS 5 gene. A vertical line between two amino acids indicates complete homology. Two points between two amino acids indicates similarity between the amino acids. A single point indicates lower similarity between the residues. A blank space between the residues shows lack of homology between them.

As shown in the FIG. 8, two stretches of highly conserved residues can be identified in C. albicans LYS1 and Y. lipolytica LYS5. The first stretch is amino acids 210–225 of LYS1 (corresponding to amino acids 198–213 of the Y. lipolytica gene); the second conserved region is found in amino acids 323–344 of LYS1 and amino acids 311–332 of LYS5. The region between residues 209–224 of C. albicans has an identical counterpart in the S. cerevisiae LYS1 gene.

Due to the high degree of homology between the above referenced amino acid sequences, these sequences are the most preferred starting point for generating the probes and primers of the present invention. Due to the degeneracy of the genetic code, the degree of homology between fungi of amino acid sequences may be significantly higher than the homology of the nucleic acids that encode the amino acid sequences. Thus, in the present invention, the sequences of inventive probes and primers are generally defined in terms of amino acid sequences that they encode. In preferred embodiments, the probes and primers are defined in terms of specific sequences that have shown homology between fungal species.

EXAMPLE 6

Conserved sequences identified by comparing the putative amino acid sequence of saccharopine dehydrogenase expressed by *C. albicans* and that expressed by *Yarrowia lipolytica* were used to develop PCR primers for the purpose of amplifying fungal genomic DNA from *Cryptococcus neoformans* (see FIG. 7) (a putative amino acid sequence for *S. cerevisiae* saccharopine dehydrogenase was not available at the time the primers were developed). The following amino acid sequences were found to be entirely conserved between the two putative sequences: HEHIQFA (SEQ ID NO:4) and DIFINCI (SEQ ID NO:10). Two oligonucleotides coding for these two conserved amino acid sequences were then synthesized as slightly degenerate PCR primers having the sequences set forth below (both are provided in the 5' to 3' orientation):

CAC GAG CAC ATC CAG TT(C or T) GC (SEQ ID: 27)
and
ATGCA GTT GAT GAA (G or A)AT (G or T)TC (SEQ ID: 28).

These primers were used to amplify a nucleic acid 549 base pairs in length from a sample of genomic DNA isolated from *Cryptococcus neoformans*. The genomic DNA was isolated from *C. neoformans* by the methods described by Minuth and coworkers (W. Minuth et al., Current Genetics 5:227–231 (1982)).

Amplification was conducted essentially as described in "PCR Protocols; a Guide to Methods and Applications" (eds. M. A. Innis, D. H. Gelfand, J. J. Sninsky and T. J. White (1990), Academic Press, Inc., New York) which is hereby incorporated by reference. Specific reaction conditions for this amplification were as follows: 50 picomoles of each primer and ~10 ng of *C. neoformans* genomic DNA were used. 1–5 units of Taq polymerase and corresponding 10× buffer was obtained from Boehringer Mannheim. A 1× solution of the Taq polymerase in buffer was made for a total volume of 100 μL. The PCR reactions were incubated in a DNA Thermal Cycler (Perkin Elmer Cetus, Emeryville, Calif.) with the following cycle parameters:

One cycle was completed as follows:
stage 1 melting temperature: 94 C., one minute
annealing temperature: 37 C., one minute
extension temperature: 72 C., two minutes
Thirty cycles were then completed using the following parameters:
stage 2 melting temperature: 94 C., thirty seconds
annealing temperature: 55 C., thirty seconds
extension temperature: 72 C., thirty seconds.

The fragment so amplified was inserted into a pBluescript KS+ sequencing vector and sequenced by the dideoxynucleotide chain termination method of Sanger (F. Sanger et al., *J. Mol. Biol.*, 94, pg. 441 (1975); F. Sanger et al., *Proc. Natl. Acad. Sci. U.S.A.*, 74 pg. 5463 (1977)). The sequence of this 549 base pair fragment (SEQ ID: 31) is set forth in FIG. 8. The underlined nucleotides at the beginning and end of the sequence represent sequences derived from the sequencing vector, pBluescript KS+. An intron is also indicated to include bases 406–469 in FIG. 8.

It is believed that this 549 base pair nucleic acid is derived from the *C. neoformans* gene for saccharopine dehydrogenase. A putative partial amino acid sequence of the *Cryptococcus neoformans* protein is set forth in FIG. 3 (SEQ ID 32). This partial sequence is based on a translation of the 549 base sequence (excluding the intron indicated in FIG. 8) identified by the present inventors. This putative sequence is compared in FIG. 3 with the putative amino acid sequences for *C. albicans*, *S. cerevisiae*, and *Y. lipolytica*. The intron in the 549 base pair fragment falls between the coding region for the amino acids at positions 233 and 234.

EXAMPLE 7

DNA isolated from a blood sample obtained from a patient suspected of harboring a Candida infection is subjected to PCR amplification. Appropriate primer pairs are selected from the following sequences for use in amplifying genetic material contained in the blood sample by means of the polymerase chain reaction:

CTTGTTATTGGTGCCTTGGGTAGATGTGGATCTGG-TGCCATTGATTTA (SEQ ID: 21)

GGTCCTAAATTATCAGTATGTTCAATTGATCATTT-ACCTTCTTTATTACCTAGAGAAGCTTCAGAA (SEQ ID: 25)

ATGCA GTT GAT GAA (G or A)AT (G or T)TC (SEQ ID: 27)

CAC GAG CAC ATC CAG TT(C or T) GC (SEQ ID: 28)

The amplified nucleic acids are transferred to a nitrocellulose filter and bound there. Fluorescently labeled nucleic acid hybridization probes homologous to at least a portion of the amplified genetic fragments are then applied in a hybridization buffer and are allowed to incubate with the DNA-harboring filter for 24 hours.

The filter is washed and probe binding is detected through fluoroscopy. Statistically significant probe binding is indicative of the presence of fungus in the biological sample.

Alternatively, the procedure described above may be conducted using primers included in the following description:

the nucleotide sequence of each member of the primer pair is a nucleotide sequence selected from the group consisting of nucleic acid sequences that code for polypeptides that are (a) derived from saccharopine dehydrogenase expressed by wild type *Candida albicans* and (b) are conserved among fungi, wherein the nucleotide sequences are not homologous to and do not cross react with nucleotide sequences found in the human genome and homologues thereof.

EXAMPLE 8

A biological sample is obtained from a patient suspected of harboring candidosis. Proteins from the sample are isolated, denatured and electrophoresed. The gel so produced is subjected to a procedure known to those of skill in the art as a Western Blot.

The proteins from the electrophoresis gel are vacuum eluted onto a nitrocellulose filter. To the filter is applied a sample of radiolabeled monoclonal antibody capable of binding selectively to the saccharopine dehydrogenase enzyme expressed by wild type *C. albicans*. The antibody is allowed to bind, after which excess antibody is removed. The filter is subjected to autoradiography and the resulting autoradiographs are interpreted to determine whether fungal proteins were present in the original biological sample.

EXAMPLE 9

A throat swab is obtained from a patient suspected of harboring a Candida infection. DNA is isolated from the sample and applied as a dot blot to a nitrocellulose filter. The filter is then treated with a high concentration salt solution and heated to bind the DNA. The filter so treated is placed in a plastic bag with prehybridization buffer.

Hybridization buffer containing radiolabeled nucleic acid hybridization probes having one of the following sequences is then applied to the filter:

CTTCATTTAAGAGCAGAAACTAAACCATTAGAA (SEQ ID: 14)
TTACTCGATGCTGGATTTGAA (SEQ ID: 15)
GGTTTAAAAGAATTACCTGAA (SEQ ID: 16)
CATGAACATATTCAATTTGCT (SEQ ID: 17)
TTATATGATTTAGAATTTTTAGAA (SEQ ID: 18)
GGTAGGAGAGTTGCTGCCTTTGGATTT (SEQ ID: 19)
GCTGGATTTGCTGGGGCTGCC (SEQ ID: 20)
CTTGTTATTGGTGCCTTGGGTAGATGTGGATCTGGTGCCATTGATTTA (SEQ ID: 21)
AAAGGTGGTCCATTCCAAGAAATT (SEQ ID: 22)
GATATTTTCATTAATTGTATT (SEQ ID: 23)
ATTGTTGATGTTTCTGCTGATACTACTAATCCTCATAATCCA (SEQ ID: 24)
GGTCCTAAATTATCAGTATGTTCAATTGATCATTTACCTTCTTTATTACCTAGAGAAGCTTCAGAA (SEQ ID: 25)
TTATTTGATAAACACGTTGCCAGA (SEQ ID: 26)
ATGCA GTT GAT GAA (G or A)AT (G or T)TC (SEQ ID: 27)
CAC GAG CAC ATC CAG TT(C or T) GC (SEQ ID: 28); nucleic acids having nucleotide sequences that code for polypeptides that are (a) derived from saccharopine dehydrogenase expressed by wild type *Candida albicans* and (b) conserved among fungi, wherein the nucleic acid hybridization probes are not homologous to and do not cross react with nucleotide sequences found in the human genome; and homologs of the sequences set forth above that will remain hybridized under relatively high stingency conditions.

The filter is incubated in the bag for approximately 24 hours. Such probes bind specifically to fungi and binding is indicative of the presence of fungal nucleic acids in the blood sample. The filter is then washed to remove unannealed probe and dried. The filter so treated is then subjected to autoradiography.

Statistically significant probe binding indicates the presence of a fungal pathogen in the sample; appropriate therapeutic intervention is then planned.

EXAMPLE 10

The procedure carried out in Example 9 is conducted in an identical fashion, with the exception that the sample utilized is a vaginal swab.

It should be understood that the foregoing disclosure emphasizes certain specific embodiments of the invention and that all modifications or alternative equivalent thereto are within the spirit or scope of the invention as set forth in the appended claims.

---

We claim:

1. An isolated and purified nucleic acid coding for a polypeptide fragment derived from saccharopine dehydrogenase expressed by *Candida albicans* and which is conserved in fungi, said nucleic acid selected from the group consisting of:
CTTCATTTAAGAGCAGAAACTAAACCATTAGAA (SEQ ID: 14)
TTACTCGATGCTGGATTTGAA (SEQ ID: 15)
GGTTTAAAAGAATTACCTGAA (SEQ ID: 16)
CATGAACATATTCAATTTTGCT (SEQ ID: 17)
TTATATGATTTAGAATTTTTAGAA (SEQ ID: 18)
GCTAGGAGAGTTGCTGCCTTTGGATTT (SEQ ID: 19)
GCTGGATTTTGCTGGGGCTGCC (SEQ ID: 20)
CTTGTTATTGGTGCCTTGGGTAGATGTGGATCTGGTGCCATTGATTTA (SEQ. ID: 21)
AAAGGTGGTCCATTCCAAGAAATT (SEQ. ID: 22)
GATATTTTCATTAATTGTATT (SEQ ID: 23)
ATTGTTGATGTTTCTGCTGATACTACTAATCCTCATAATCCA (SEQ ID: 24)
GGTCCTAAATTATCAGTATGTTCAATTGATCATTTACCTTCTTTATTACCTGAGAAGCTTCAGAA (SEQ ID: 25)
TTATTTGATAAACACGTTGCCAGA (SEQ ID: 26)
ATGCA GTT GAT GAA (G OR A)AT (G OR T)TC (SEQ ID: 27)
CAC GAG CAC ATC CAG TT (C OR T) GC (SEQ ID: 28).

2. A nucleic acid hybridization probe of from about 15 bases to about 400 bases comprising an isolated and purified nucleic acid coding for a polypeptide fragment derived from saccharopine dehydrogenase expressed by *Candida albicans*, said nucleic acid selected from the group consisting of:
CTTCATTTAAGAGCAGAAACTAAACCATTAGAA (SEQ ID: 14)
TTACTCGATGCTGGATTTGAA (SEQ ID: 15)
GGTTTAAAAGAATTACCTGAA (SEQ ID: 16)
CATGAACATATTCAATTTTGCT (SEQ ID: 17)
TTATATGATTTAGAATTTTTAGAA (SEQ ID: 18)
GCTAGGAGAGTTGCTGCCTTTGGATTT (SEQ ID: 19)
GCTGGATTTTGCTGGGGCTGCC (SEQ ID: 20)
CTTGTTATTGGTGCCTTGGGTAGATGTGGATCTGGTGCCATTGATTTA (SEQ. ID: 21)
AAAGGTGGTCCATTCCAAGAAATT (SEQ. ID: 22)
GATATTTTCATTAATTGTATT (SEQ ID: 23)
ATTGTTGATGTTTCTGCTGATACTACTAATCCTCATAATCCA (SEQ ID: 24)
GGTCCTAAATTATCAGTATGTTCAATTGATCATTTACCTTCTTTATTACCTGAGAAGCTTCAGAA (SEQ ID:25)
TTATTTGATAAACACGTTGCCAGA (SEQ ID: 26)
ATGCA GTT GAT GAA (G OR A)AT (G OR T)TC (SEQ ID: 27)
CAC GAG CAC ATC CAG TT (C OR T) GC (SEQ ID: 28).

3. A hybridization probe of claim 1 wherein the probe is a labeled probe.

4. A method of screening a biological sample for the presence of a fungal pathogen, the method comprising hybridizing a nucleic acid isolated from the biological sample with a hybridization probe of claim 2; and detecting the hybridized probe.

5. A method of screening a biological sample for the presence of a fungal pathogen comprising
  (i) hybridizing a nucleic acid isolated from the biological sample with a nucleic acid hybridization probe of claim 2; and
  (ii) detecting the hybridized probe.

6. The method of claim 5 wherein steps (i) and (ii) performed by machine.

7. The method of claim 2 wherein the hybridization is carried out on a filter.

8. The method of claim 2 wherein the hybridization is carried out in solution.

9. The method of claim 2 wherein hybridization is detected by autoradiography.

10. The method of claim 2 wherein the nucleic acid is isolated from the biological sample prior to hybridization with the hybridization probe.

11. The method of claim 2 wherein the hybridization probe is applied directly to a biological sample.

12. A kit for detecting a fungal pathogen in a biological sample comprising a hybridization probe of claim 2.

13. A reagent for detecting the presence of a fungal pathogen in a biological sample comprising a hybridization probe of claim 2.

14. A pair of nucleic acid primers, each member of the pair having up to 66 bases and having a nucleotide sequence selected from the group consisting of:
CTTCATTTAAGAGCAGAAACTAAACCATTAGAA (SEQ ID: 14)
TTACTCGATGCTGGATTTGAA (SEQ ID: 15)
GGTTTAAAAGAATTACCTGAA (SEQ ID: 16)
CATGAACATATTCAATTTTGCT (SEQ ID: 17)
TTATATGATTTAGAATTTTTAGAA (SEQ ID: 18)
GCTAGGAGAGTTGCTGCCTTTGGATTT (SEQ ID: 19)
GCTGGATTTTGCTGGGGCTGCC (SEQ ID: 20)
CTTGTTATTGGTGCCTTGGGTAGATGTGGATCTGGTGCCATTGATTTA (SEQ. ID: 21)
AAAGGTGGTCCATTCCAAGAAATT (SEQ. ID: 22)
GATATTTTCATTAATTGTATT (SEQ ID: 23)
ATTGTTGATGTTTCTGCTGATACTACTAATCCTCATAATCCA (SEQ ID: 24)

GGTCCTAAATTATCAGTATGTTCAATTGATCATTT-ACCTTCTTTATTACCTGAGAAGCTTCAGAA (SEQ ID: 25)
TTATTTGATAAACACGTTGCCAGA (SEQ ID: 26)
ATGCA GTT GAT GAA (G OR A)AT (G OR T)TC (SEQ ID: 27)
CAC GAG CAC ATC CAG TT (C OR T) GC (SEQ ID: 28).

15. A method of screening a biological sample for the presence of a fungal pathogen comprising:
(i) hybridizing a hybridization probe to an amplified sample of genetic material, wherein the genetic material is amplified using nucleic acid primer pairs each member of the pair having a nucleotide sequence selected from the group consisting of
CTTCATTTAAGAGCAGAAACTAAACCATTAGAA (SEQ ID: 14)
TTACTCGATGCTGGATTTGAA (SEQ ID: 15)
GGTTTAAAAGAATTACCTGAA (SEQ ID: 16)
CATGAACATATTCAATTTTGCT (SEQ ID: 17)
TTATATGATTTAGAATTTTTAGAA (SEQ ID: 18)
GCTAGGAGAGTTGCTGCCTTTGGATTT (SEQ ID: 19)
GCTGGATTTTGCTGGGGCTGCC (SEQ ID: 20)
CTTGTTATTGGTGCCTTGGGTAGATGTGGATCTGG-TGCCATTGATTTA (SEQ. ID: 21)
AAAGGTGGTCCATTCCAAGAAATT (SEQ. ID: 22)
GATATTTTCATTAATTGTATT (SEQ ID: 23)
ATTGTTGATGTTTCTGCTGATACTACTAATCCTCAT-AATCCA (SEQ ID: 24)
GGTCCTAAATTATCAGTATGTTCAATTGATCATTT-ACCTTCTTTATTACCTGAGAAGCTTCAGAA (SEQ ID: 25)
TTATTTGATAAACACGTTGCCAGA (SEQ ID: 26)
ATGCA GTT GAT GAA (G OR A)AT (G OR T)TC (SEQ ID: 27)
CAC GAG CAC ATC CAG TT (C OR T) GC (SEQ ID: 28); and
(ii) detecting the hybridized probe.

16. The method of claim 15 wherein the hybridization conducted on a filter.

17. The method of claim 15 wherein the hybridization is conducted in solution.

18. The method of claim 15 wherein hybridization is detected by autoradiography.

19. The method of claim 15 wherein the method is performed by a machine.

20. A reagent for detecting the presence of a fungal pathogen in a biological sample comprising the nucleic acid primers of claim 14.

21. A kit for detecting the presence of a fungal pathogen in a biological sample comprising the nucleic acid primers of claim 14.

22. A method for identifying restriction fragment length polymorphisms in nucleic acid isolated from a biological sample comprising the steps of:
(i) providing the hybridization probe of claim 2 and nucleic acid isolated from a biological sample and digested;
(ii) hybridizing the hybridization probe with the nucleic acid; and
(iii) detecting the hybridized probe.

* * * * *

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
       (A) LENGTH: 11 amino acid residues
       (B) TYPE: amino acid
       (D) TOPOLOGY: linear (ii) MOLECULE TYPE:
       (A) DESCRIPTION: peptide (iii) HYPOTHETICAL: Yes (v) FRAGMENT TYPE: internal fragment (vi) ORIGINAL SOURCE:
       (A) ORGANISM: Saccharomyces cerevisiae (xi) SEQUENCE DESCRIPTION: SEQ ID NO:1:

Leu His Leu Arg Ala Glu Thr Lys Pro Leu Glu
1               5                   10

(2) INFORMATION FOR SEQ ID NO:2:

(i) SEQUENCE CHARACTERISTICS:
       (A) LENGTH: 7 amino acid residues
       (B) TYPE: amino acid
       (D) TOPOLOGY: linear (ii) MOLECULE TYPE:
       (A) DESCRIPTION: peptide (iii) HYPOTHETICAL: Yes (v) FRAGMENT TYPE: internal fragment (vi) ORIGINAL SOURCE:
       (A) ORGANISM: Saccharomyces cerevisiae (xi) SEQUENCE DESCRIPTION: SEQ ID NO:2:

Leu Leu Asp Ala Gly Phe Glu
1               5

(2) INFORMATION FOR SEQ ID NO:3:

(i) SEQUENCE CHARACTERISTICS:
            (A) LENGTH: 7 amino acid residues
            (B) TYPE: amino acid
            (D) TOPOLOGY: linear (ii) MOLECULE TYPE:
            (A) DESCRIPTION: peptide (iii) HYPOTHETICAL: Yes (v) FRAGMENT TYPE: internal fragment (vi) ORIGINAL SOURCE:
            (A) ORGANISM: Saccharomyces cerevisiae (xi) SEQUENCE DESCRIPTION: SEQ ID NO:3:

Gly Leu Lys Glu Leu Pro Glu
1               5

(2) INFORMATION FOR SEQ ID NO:4:

(i) SEQUENCE CHARACTERISTICS:
            (A) LENGTH: 7 amino acid residues
            (B) TYPE: amino acid
            (D) TOPOLOGY: linear (ii) MOLECULE TYPE:
            (A) DESCRIPTION: peptide (iii) HYPOTHETICAL: Yes (v) FRAGMENT TYPE: internal fragment (vi) ORIGINAL SOURCE:
            (A) ORGANISM: Saccharomyces cerevisiae (xi) SEQUENCE DESCRIPTION: SEQ ID NO:4:

His Glu His Ile Gln Phe Ala
1               5

(2) INFORMATION FOR SEQ ID NO:5:

(i) SEQUENCE CHARACTERISTICS:
            (A) LENGTH: 8 amino acid residues
            (B) TYPE: amino acid
            (D) TOPOLOGY: linear (ii) MOLECULE TYPE:
            (A) DESCRIPTION: peptide (iii) HYPOTHETICAL: Yes (v) FRAGMENT TYPE: internal fragment (vi) ORIGINAL SOURCE:
            (A) ORGANISM: Saccharomyces cerevisiae (xi) SEQUENCE DESCRIPTION: SEQ ID NO:5:

Leu Tyr Asp Leu Glu Phe Leu Glu
1               5

(2) INFORMATION FOR SEQ ID NO:6:

(i) SEQUENCE CHARACTERISTICS:
            (A) LENGTH: 9 amino acid residues
            (B) TYPE: amino acid (D) TOPOLOGY: linear (ii) MOLECULE TYPE:
            (A) DESCRIPTION: peptide (iii) HYPOTHETICAL: Yes (v) FRAGMENT TYPE: internal fragment (vi) ORIGINAL SOURCE:
            (A) ORGANISM: Saccharomyces cerevisiae (xi) SEQUENCE DESCRIPTION: SEQ ID NO:6:

Gly Arg Arg Val Ala Ala Phe Gly Phe
1               5

(2) INFORMATION FOR SEQ ID NO:7:

(i) SEQUENCE CHARACTERISTICS:
            (A) LENGTH: 10 amino acid residues
            (B) TYPE: amino acid
            (D) TOPOLOGY: linear (ii) MOLECULE TYPE:
            (A) DESCRIPTION: peptide (iii) HYPOTHETICAL: Yes (v) FRAGMENT TYPE: internal fragment (vi) ORIGINAL SOURCE:
            (A) ORGANISM: Saccharomyces cerevisiae (xi) SEQUENCE DESCRIPTION: SEQ ID NO:7:

Ala Gly Phe Ala Gly Ala Ala Ile Gly Val
1               5                   10

(2) INFORMATION FOR SEQ ID NO:8:

(i) SEQUENCE CHARACTERISTICS:
            (A) LENGTH: 16 amino acid residues
            (B) TYPE: amino acid
            (D) TOPOLOGY: linear (ii) MOLECULE TYPE:
            (A) DESCRIPTION: peptide (iii) HYPOTHETICAL: Yes (v) FRAGMENT TYPE: internal fragment (vi) ORIGINAL SOURCE:
            (A) ORGANISM: Saccharomyces cerevisiae (xi) SEQUENCE DESCRIPTION: SEQ ID NO:8:

Leu Val Ile Gly Ala Leu Gly Arg Cys Gly Ser Gly Ala Ile Asp
1               5                   10                  15

Leu (2) INFORMATION FOR SEQ ID NO:9:

(i) SEQUENCE CHARACTERISTICS:
            (A) LENGTH: 8 amino acid residues
            (B) TYPE: amino acid
            (D) TOPOLOGY: linear (ii) MOLECULE TYPE:
            (A) DESCRIPTION: peptide (iii) HYPOTHETICAL: Yes (v) FRAGMENT TYPE: internal fragment (vi) ORIGINAL SOURCE:
                 (A) ORGANISM: Saccharomyces cerevisiae (xi) SEQUENCE DESCRIPTION: SEQ ID NO:9:

Lys Gly Gly Pro Phe Gln Glu Ile
1               5

(2) INFORMATION FOR SEQ ID NO:10:

(i) SEQUENCE CHARACTERISTICS:
             (A) LENGTH: 7 amino acid residues
             (B) TYPE: amino acid
             (D) TOPOLOGY: linear (ii) MOLECULE TYPE:
             (A) DESCRIPTION: peptide (iii) HYPOTHETICAL: Yes (v) FRAGMENT TYPE: internal fragment (vi) ORIGINAL SOURCE:
             (A) ORGANISM: Saccharomyces cerevisiae (xi) SEQUENCE DESCRIPTION: SEQ ID NO:10:

Asp Ile Phe Ile Asn Cys Ile
1               5

(2) INFORMATION FOR SEQ ID NO:11:

(i) SEQUENCE CHARACTERISTICS:
             (A) LENGTH: 14 amino acid residues
             (B) TYPE: amino acid
             (D) TOPOLOGY: linear (ii) MOLECULE TYPE:
             (A) DESCRIPTION: peptide (iii) HYPOTHETICAL: Yes (v) FRAGMENT TYPE: internal fragment (vi) ORIGINAL SOURCE:
             (A) ORGANISM: Saccharomyces cerevisiae (xi) SEQUENCE DESCRIPTION: SEQ ID NO:11:

Ile Val Asp Val Ser Ala Asp Thr Thr Asn Pro His Asn Pro
1               5                   10

(2) INFORMATION FOR SEQ ID NO:12:

(i) SEQUENCE CHARACTERISTICS:
             (A) LENGTH: 22 amino acid residues
             (B) TYPE: amino acid
             (D) TOPOLOGY: linear (ii) MOLECULE TYPE:
             (A) DESCRIPTION: peptide (iii) HYPOTHETICAL: Yes (v) FRAGMENT TYPE: internal fragment (vi) ORIGINAL SOURCE:
             (A) ORGANISM: Saccharomyces cerevisiae (xi) SEQUENCE DESCRIPTION: SEQ ID NO:12:

Gly Pro Lys Leu Ser Val Cys Ser Ile Asp His Leu Pro Ser Leu
1               5                   10                  15

Leu Pro Arg Glu Ala Ser Glu
                20

(2) INFORMATION FOR SEQ ID NO:13:

(i) SEQUENCE CHARACTERISTICS:
        (A) LENGTH: 8 amino acid residues
        (B) TYPE: amino acid
        (D) TOPOLOGY: linear (ii) MOLECULE TYPE:
        (A) DESCRIPTION: peptide (iii) HYPOTHETICAL: Yes (v) FRAGMENT TYPE: internal fragment (vi) ORIGINAL SOURCE:
        (A) ORGANISM: Saccharomyces cerevisiae (xi) SEQUENCE DESCRIPTION: SEQ ID NO:13:

```
Leu Phe Asp Lys His Val Ala Arg
1               5
```

(2) INFORMATION FOR SEQ ID NO:14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (iii) HYPOTHETICAL: NO (vi) ORIGINAL SOURCE:
        (A) ORGANISM: Saccharomyces cerevisiae (xi) SEQUENCE DESCRIPTION: SEQ ID NO:14:

```
CTT CAT TTA AGA GCA GAA ACT AAA CCA TTA GAA          33
Leu His Leu Arg Ala Glu Thr Lys Pro Leu Glu
1               5                   10
```

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (vi) ORIGINAL SOURCE:
        (A) ORGANISM: Saccharomyces cerevisiae (xi) SEQUENCE DESCRIPTION: SEQ ID NO:15:

```
TTA CTC GAT GCT GGA TTT GAA                          21
Leu Leu Asp Ala Gly Phe Glu
1               5
```

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (vi) ORIGINAL SOURCE:
        (A) ORGANISM: Saccharomyces cerevisiae (xi) SEQUENCE DESCRIPTION: SEQ ID NO:16:

```
GGT TTA AAA GAA TTA CCT GAA                          21
```

```
Gly Leu Lys Glu Leu Pro Glu
1               5
```

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (vi) ORIGINAL SOURCE:
        (A) ORGANISM: Saccharomyces cerevisiae (xi) SEQUENCE DESCRIPTION: SEQ ID NO:17:

```
CAT GAA CAT ATT CAA TTT GCT                                     21
His Glu His Ile Gln Phe Ala
1               5
```

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (iii) HYPOTHETICAL: NO (vi) ORIGINAL SOURCE:
        (A) ORGANISM: Saccharomyces cerevisiae (xi) SEQUENCE DESCRIPTION: SEQ ID NO:18:

```
TTA TAT GAT TTA GAA TTT TTA GAA                                 24
Leu Tyr Asp Leu Glu Phe Leu Glu
1               5
```

(2) INFORMATION FOR SEQ ID NO:19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (iii) HYPOTHETICAL: NO (vi) ORIGINAL SOURCE:
        (A) ORGANISM: Saccharomyces cerevisiae (xi) SEQUENCE DESCRIPTION: SEQ ID NO:19:

```
GGT AGG AGA GTT GCT GCC TTT GGA TTT                             27
Gly Arg Arg Val Ala Ala Phe Gly Phe
1               5
```

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (vi) ORIGINAL SOURCE:
        (A) ORGANISM: Saccharomyces cerevisiae (xi) SEQUENCE DESCRIPTION: SEQ ID NO:20:

```
GCT GGA TTT GCT GGG GCT GCC                                     21
```

```
Ala Gly Phe Ala Gly Ala Ala
1               5
```

(2) INFORMATION FOR SEQ ID NO:21:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (iii) HYPOTHETICAL: NO (vi) ORIGINAL SOURCE:
        (A) ORGANISM: Saccharomyces cerevisiae (xi) SEQUENCE DESCRIPTION: SEQ ID NO:21:

```
CTT GTT ATT GGT GCC TTG GGT AGA TGT GGA TCT GGT GCC           39
Leu Val Ile Gly Ala Leu Gly Arg Cys Gly Ser Gly Ala
1               5                   10

ATT GAT TTA                                                   48
Ile Asp Leu
        15
```

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (iii) HYPOTHETICAL: NO (vi) ORIGINAL SOURCE:
        (A) ORGANISM: Saccharomyces cerevisiae (xi) SEQUENCE DESCRIPTION: SEQ ID NO:22:

```
AAA GGT GGT CCA TTC CAA GAA ATT                               24
Lys Gly Gly Pro Phe Gln Glu Ile
1               5
```

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (vi) ORIGINAL SOURCE:
        (A) ORGANISM: Saccharomyces cerevisiae (xi) SEQUENCE DESCRIPTION: SEQ ID NO:23:

```
GAT ATT TTC ATT AAT TGT ATT                                   21
Asp Ile Phe Ile Asn Cys Ile
1               5
```

(2) INFORMATION FOR SEQ ID NO:24:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (iii) HYPOTHETICAL: NO (xi) SEQUENCE DESCRIPTION: SEQ ID NO:24:

```
ATT GTT GAT GTT TCT GCT GAT ACT ACT AAT CCT CAT AAT CCA      42
Ile Val Asp Val Ser Ala Asp Thr Thr Asn Pro His Asn Pro
1               5                   10
```

(2) INFORMATION FOR SEQ ID NO:25:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (iii) HYPOTHETICAL: NO (vi) ORIGINAL SOURCE:
        (A) ORGANISM: Saccharomyces cerevisiae (xi) SEQUENCE DESCRIPTION: SEQ ID NO:25:

```
GGT CCT AAA TTA TCA GTA TGT TCA ATT GAT CAT TTA CCT TCT TTA      45
Gly Pro Lys Leu Ser Val Cys Ser Ile Asp His Leu Pro Ser Leu
1               5                   10                  15

TTA CCT AGA GAA GCT TCA GAA                                      66
Leu Pro Arg Glu Ala Ser Glu
                20
```

(2) INFORMATION FOR SEQ ID NO:26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (iii) HYPOTHETICAL: NO (vi) ORIGINAL SOURCE:
        (A) ORGANISM: Saccharomyces cerevisiae (xi) SEQUENCE DESCRIPTION: SEQ ID NO:26:

```
TTA TTT GAT AAA CAC GTT GCC AGA                                  24
Leu Phe Asp Lys His Val Ala Arg
1               5
```

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: YES (xi) SEQUENCE DESCRIPTION: SEQ ID NO:27:

```
ATG CAG TTG ATG AAR ATK TC                                       20
```

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (xi) SEQUENCE DESCRIPTION: SEQ ID NO:28:

```
CAC GAG CAC ATC CAG TTY GC                                              20
His Glu His Ile Gln Phe Ala
 1               5
```

(2) INFORMATION FOR SEQ ID NO:29:

(i) SEQUENCE CHARACTERISTICS:
        (A) LENGTH: 1856 base pairs
        (B) TYPE: nucleic acid
        (C) STRANDEDNESS: single
        (D) TOPOLOGY: linear (iii) HYPOTHETICAL: NO (vi) ORIGINAL SOURCE:
        (A) ORGANISM: Saccharomyces cerevisiae (xi) SEQUENCE DESCRIPTION: SEQ ID NO:29:

```
CTAGTGGATC CCCCGGGCTG CAGGAATTCT TCTTCTTTTC TCCGTCTGAC                   50

TCATTTTAAT CGTCTGGTGG CTGGTGGCTG GTGGCTGGCG GCGGCACGGG                  100

CAGCGGCAGC GGTGATGAGT GTGAGTTCCT TAATTATCGC CGCATGTTAT                  150

GTCGCCGTCG CCACTACTCA CACTCAAGGA ATTAATAGCG GCGTACAATA                  200

TACTCACTCA CTCACAAACA CTTTAGACGG AATTATCTCT GTCTCTCTCT                  250

CTCTGTCTCT CTCTCTTTCT CACTTAGAGA ATATATAAAC CACATTACAA                  300

TTCATTTATT CTACATTGAA CAATTTGAAT GAAAAAAAAA AAAACATTTT                  350

ATACCTTTAC TTCTTACTTC TTTCTAATAA TCAACTATAC TAGCTAACTC                  400

ATATACTAAT T ATG TCT AAA TCA CCA GTT ATT CTT CAT TTA AGA                444
             Met Ser Lys Ser Pro Val Ile Leu His Leu Arg
              1               5                  10

GCA GAA ACT AAA CCA TTA GAA GCT AGA GCT GCT TTA ACT CCT                 486
Ala Glu Thr Lys Pro Leu Glu Ala Arg Ala Ala Leu Thr Pro
         15                  20                  25

TCT ACT ACT AAA CAA TTA CTC GAT GCT GGA TTT GAA ATT TAT                 528
Ser Thr Thr Lys Gln Leu Leu Asp Ala Gly Phe Glu Ile Tyr
             30                  35

GTT GAA GAA TCT TCT CAA TCT ACT TTT GAT ATT AAA GAA TAT                 570
Val Glu Glu Ser Ser Gln Ser Thr Phe Asp Ile Lys Glu Tyr
 40              45                  50

GAA GCT GTT GGT GCT AAA ATA GTA CCT GAA GGT TCA TGG AAA                 612
Glu Ala Val Gly Ala Lys Ile Val Pro Glu Gly Ser Trp Lys
     55                  60                  65

ACT GCT CCT AAA GAG AGA ATT ATT TTT GGT TTA AAA GAA TTA                 654
Thr Ala Pro Lys Glu Arg Ile Ile Phe Gly Leu Lys Glu Leu
         70                  75                  80

CCT GAA AAT GAA ACT TTC CCA TTA ATT CAT GAA CAT ATT CAA                 696
Pro Glu Asn Glu Thr Phe Pro Leu Ile His Glu His Ile Gln
             85                  90                  95

TTT GCT CAT TGT TAT AAA GAT CAA GCT GGT TGG CAA GAT GTT                 738
Phe Ala His Cys Tyr Lys Asp Gln Ala Gly Trp Gln Asp Val
                100                 105

TTA AAA AGA TTC CCA CAA GGT AAT GGT ATA TTA TAT GAT TTA                 780
Leu Lys Arg Phe Pro Gln Gly Asn Gly Ile Leu Tyr Asp Leu
110                 115                 120

GAA TTT TTA GAA AAT GAT CAA GGT AGG AGA GTT GCT GCC TTT                 822
Glu Phe Leu Glu Asn Asp Gln Gly Arg Arg Val Ala Ala Phe
        125                 130                 135

GGA TTT TAT GCT GGA TTT GCT GGG GCT GCC ATT GGG GTA TTA                 864
Gly Phe Tyr Ala Gly Phe Ala Gly Ala Ala Ile Gly Val Leu
                140                 145                 150
```

| | |
|---|---|
| GAT TGG AGT TTT AAA CAA TTG AAT GGT AAT ACT AAA GGT ACT<br>Asp Trp Ser Phe Lys Gln Leu Asn Gly Asn Thr Lys Gly Thr<br>155                    160                    165 | 906 |
| AAA GGT GAA GGT GAA GGT GGT GAA TTA CCT GGG GTG ACT CCA<br>Lys Gly Glu Gly Glu Gly Gly Glu Leu Pro Gly Val Thr Pro<br>                170                    175 | 948 |
| TAT CCT AAT GAA AAT GAA TTA ATT AAA GAT GTT AAA ATT GAA<br>Tyr Pro Asn Glu Asn Glu Leu Ile Lys Asp Val Lys Ile Glu<br>180                    185                    190 | 990 |
| TTA GAA AAA GCT TTA ACT AAA AAT GGG GGT CAA TAT CCT AAA<br>Leu Glu Lys Ala Leu Thr Lys Asn Gly Gly Gln Tyr Pro Lys<br>     195                   200                    205 | 1032 |
| TGT CTT GTT ATT GGT GCC TTG GGT AGA TGT GGA TCT GGT GCC<br>Cys Leu Val Ile Gly Ala Leu Gly Arg Cys Gly Ser Gly Ala<br>            210                    215                    220 | 1074 |
| ATT GAT TTA TTT AAA AAA ATT GGT ATC CCT GAT GAT AAT ATT<br>Ile Asp Leu Phe Lys Lys Ile Gly Ile Pro Asp Asp Asn Ile<br>                  225                    230                    235 | 1116 |
| GCT AAA TGG GAT ATG GCT GAA ACT GCT AAA GGT GGT CCA TTC<br>Ala Lys Trp Asp Met Ala Glu Thr Ala Lys Gly Gly Pro Phe<br>                      240                    245 | 1158 |
| CAA GAA ATT GTT GAT CTG GAT ATT TTC ATT AAT TGT ATT TAT<br>Gln Glu Ile Val Asp Leu Asp Ile Phe Ile Asn Cys Ile Tyr<br>250                    255                    260 | 1200 |
| TTA TCT AAA CCA ATC CCA CCA TTT ATT AAT AAA GAA ATT TTG<br>Leu Ser Lys Pro Ile Pro Pro Phe Ile Asn Lys Glu Ile Leu<br>     265                   270                    275 | 1242 |
| TTA TTA CTA AAT AGA AAA TTG ACT ACT ATT GTT GAT GTT TCT<br>Asn Asn Glu Asn Arg Lys Leu Thr Thr Ile Val Asp Val Ser<br>            280                    285                    290 | 1284 |
| GCT GAT ACT ACT AAT CCT CAT AAT CCA ATC CCA GTA TAT GAA<br>Ala Asp Thr Thr Asn Pro His Asn Pro Ile Pro Val Tyr Glu<br>                  295                    300                    305 | 1326 |
| ATT GCT ACA GTT TTC AAT GAA CCA ACC GTT GAA GTT AAA CTT<br>Ile Ala Thr Val Phe Asn Glu Pro Thr Val Glu Val Lys Leu<br>                      310                    315 | 1368 |
| GAT AAA GGT CCT AAA TTA TCA GTA TGT TCA ATT GAT CAT TTA<br>Asp Lys Gly Pro Lys Leu Ser Val Cys Ser Ile Asp His Leu<br>320                    325                    330 | 1410 |
| CCT TCT TTA TTA CCT AGA GAA GCT TCA GAA TTT TTT GCT AAA<br>Pro Ser Leu Leu Pro Arg Glu Ala Ser Glu Phe Phe Ala Lys<br>     335                   340                    345 | 1452 |
| GAT TTA ATG CCA TCA TTA TTG GAA TTA CCA AAT AGA GAT ACT<br>Asp Leu Met Pro Ser Leu Leu Glu Leu Pro Asn Arg Asp Thr<br>            350                    355                    360 | 1494 |
| TCT CCA GTA TGG GTT AGA GCT AAA CAA TTA TTT GAT AAA CAC<br>Ser Pro Val Trp Val Arg Ala Lys Gln Leu Phe Asp Lys His<br>                  365                    370                    375 | 1536 |
| GTT GCC AGA CTT GAT AAA GAG TAGTAGTAGG TTTACAAGT<br>Val Ala Arg Leu Asp Lys Glu<br>            380 | 1576 |
| CAAGTAAATG TGTTAATAA ATATTTTATT AAATCTTTTA TTTTATTTTA | 1626 |
| TTTCATTTCA TTTCTTAATT AGTATCTGTG TATATTGGGA TCTATTAGTA | 1676 |
| AAATAGTAGC ACTATTATTA TTCTAATGTT ACACTAACTT TTCTTTTCTT | 1726 |
| TTTAATATTA TTCTTTTTTG ATTTCTTACC CTTTTTATTC TTTTCACCTT | 1776 |
| GCATTATATT TTTAATTTCT TCACCATCAG TTTCATATTC AGATTCACTA | 1826 |
| GGGATATCAA GCTTATCGAT ACCGTCGACC | 1856 |

(2) INFORMATION FOR SEQ ID NO:30:

(i) SEQUENCE CHARACTERISTICS:
        (A) LENGTH: 382 amino acid residues
        (B) TYPE: amino acid
        (D) TOPOLOGY: linear (ii) MOLECULE TYPE:
        (A) DESCRIPTION: protein (iii) HYPOTHETICAL: Yes (vi) ORIGINAL SOURCE:
        (A) ORGANISM: Candida albicans (xi) SEQUENCE DESCRIPTION: SEQ ID NO:30:

```
Met Ser Lys Ser Pro Val Ile Leu His Leu Arg Ala Glu Thr Lys
1               5                   10                  15

Pro Leu Glu Ala Arg Ala Ala Leu Thr Pro Ser Thr Thr Lys Gln
            20                  25                  30

Leu Leu Asp Ala Gly Phe Glu Ile Tyr Val Glu Glu Ser Ser Gln
            35                  40                  45

Ser Thr Phe Asp Ile Lys Glu Tyr Glu Ala Val Gly Ala Lys Ile
            50                  55                  60

Val Pro Glu Gly Ser Trp Lys Thr Ala Pro Lys Glu Arg Ile Ile
            65                  70                  75

Phe Gly Leu Lys Glu Leu Pro Glu Asn Glu Thr Phe Pro Leu Ile
            80                  85                  90

His Glu His Ile Gln Phe Ala His Cys Tyr Lys Asp Gln Ala Gly
            95                  100                 105

Trp Gln Asp Val Leu Lys Arg Phe Pro Gln Gly Asn Gly Ile Leu
            110                 115                 120

Tyr Asp Leu Glu Phe Leu Glu Asn Asp Gln Gly Arg Arg Val Ala
            125                 130                 135

Ala Phe Gly Phe Tyr Ala Gly Phe Ala Gly Ala Ile Gly Val
            140                 145                 150

Leu Asp Trp Ser Phe Lys Gln Leu Asn Gly Asn Thr Lys Gly Thr
            155                 160                 165

Lys Gly Glu Gly Glu Gly Gly Glu Leu Pro Gly Val Thr Pro Tyr
            170                 175                 180

Pro Asn Glu Asn Glu Leu Ile Lys Asp Val Lys Ile Glu Leu Glu
            185                 190                 195

Lys Ala Leu Thr Lys Asn Gly Gly Gln Tyr Pro Lys Cys Leu Val
            200                 205                 210

Ile Gly Ala Leu Gly Arg Cys Gly Ser Gly Ala Ile Asp Leu Phe
            215                 220                 225

Lys Lys Ile Gly Ile Pro Asp Asp Asn Ile Ala Lys Trp Asp Met
            230                 235                 240

Ala Glu Thr Ala Lys Gly Gly Pro Phe Gln Glu Ile Val Asp Leu
            245                 250                 255

Asp Ile Phe Ile Asn Cys Ile Tyr Leu Ser Lys Phe Ile Phe Pro
            260                 265                 270

Phe Ile Asn Lys Glu Ile Leu Asn Asn Glu Asn Arg Lys Leu Thr
            275                 280                 285

Thr Ile Val Asp Val Ser Ala Asp Thr Thr Asn Pro His Asp Pro
            290                 295                 300

Ile Pro Val Tyr Glu Ile Ala Thr Val Phe Asn Glu Phe Thr Val
            305                 310                 315
```

-continued

```
Glu Val Lys Leu Asp Lys Gly Phe Lys Leu Ser Val Cys Ser Ile
                320                 325                 330

Asp His Leu Pro Ser Leu Leu Pro Arg Glu Ala Ser Glu Phe Phe
                335                 340                 345

Ala Lys Asp Leu Met Pro Ser Leu Leu Glu Leu Phe Asn Arg Asp
                350                 355                 360

Thr Ser Pro Val Trp Val Arg Ala Lys Gln Leu Phe Asp Lys His
                365                 370                 375

Val Ala Arg Leu Asp Lys Glu
                380
```

(2) INFORMATION FOR SEQ ID NO:31:

(i) SEQUENCE CHARACTERISTICS:
        (A) LENGTH:372   amino acid residues
        (B) TYPE: amino acid
        (D) TOPOLOGY: linear (ii) MOLECULE TYPE:
        (A) DESCRIPTION: protein (iii) HYPOTHETICAL: Yes (vi) ORIGINAL SOURCE:
        (A) ORGANISM: Saccharomyces cerevisiae (xi) SEQUENCE DESCRIPTION: SEQ ID NO:31:

```
Met Ala Ala Val Thr Leu His Leu Arg Ala Glu Thr Lys Pro Leu
1               5                   10                  15

Glu Ala Arg Ala Ala Leu Thr Pro Thr Thr Val Lys Lys Leu Ile
                20                  25                  30

Ala Lys Gly Phe Lys Ile Tyr Val Glu Asp Ser Pro Gln Ser Thr
                35                  40                  45

Phe Asn Ile Asn Glu Tyr Arg Gln Ala Gly Ala Ile Ile Val Pro
                50                  55                  60

Ala Gly Ser Trp Lys Thr Ala Pro Arg Asp Arg Ile Ile Ile Gly
                65                  70                  75

Leu Lys Glu Met Pro Glu Thr Asp Thr Phe Pro Leu Val His Glu
                80                  85                  90

His Ile Gln Phe Ala His Cys Tyr Lys Asp Gln Ala Gly Trp Gln
                95                  100                 105

Asn Val Leu Met Arg Phe Ile Lys Gly Ala Gly Thr Leu Tyr Asp
                110                 115                 120

Leu Glu Phe Leu Glu Asn Asp Gln Gly Arg Arg Val Ala Ala Phe
                125                 130                 135

Gly Phe Tyr Ala Gly Phe Ala Gly Ala Ala Leu Gly Val Arg Asp
                140                 145                 150

Trp Ala Phe Lys Gln Thr His Ser Asp Asp Glu Asp Leu Pro Ala
                155                 160                 165

Val Ser Pro Tyr Pro Asn Glu Lys Ala Leu Val Lys Asp Val Thr
                170                 175                 180

Lys Asp Tyr Lys Glu Ala Leu Ala Thr Gly Ala Arg Lys Pro Thr
                185                 190                 195

Val Leu Ile Ile Gly Ala Leu Gly Arg Cys Gly Ser Gly Ala Ile
                200                 205                 210

Asp Leu Leu His Lys Val Gly Ile Pro Asp Ala Asn Ile Leu Trp
                215                 220                 225
```

-continued

```
Asp Ile Lys Glu Thr Ser Arg Gly Gly Pro Phe Asp Glu Ile Pro
                230                 235                 240

Gln Ala Asp Ile Phe Ile Asn Cys Ile Tyr Leu Ser Lys Pro Ile
            245                 250                 255

Ala Pro Phe Thr Asn Met Glu Lys Leu Asn Asn Pro Asn Arg Arg
        260                 265                 270

Leu Arg Thr Val Val Asp Val Ser Ala Asp Thr Thr Asn Pro His
    275                 280                 285

Asn Pro Ile Pro Ile Tyr Thr Val Ala Thr Val Phe Asn Lys Pro
290                 295                 300

Thr Val Leu Val Pro Thr Thr Val Gly Pro Lys Leu Ser Val Ile
            305                 310                 315

Ser Ile Asp His Leu Pro Ser Leu Leu Pro Arg Glu Ala Ser Glu
        320                 325                 330

Phe Phe Ser His Asp Leu Leu Pro Ser Leu Glu Leu Leu Pro Gln
    335                 340                 345

Arg Lys Thr Ala Pro Val Trp Val Arg Ala Lys Lys Leu Phe Asp
350                 355                 360

Arg His Cys Ala Arg Val Lys Arg Ser Ser Arg Leu
            365                 370
```

(2) INFORMATION FOR SEQ ID NO:32:

(i) SEQUENCE CHARACTERISTICS:
        (A) LENGTH: 370 amino acid residues
        (B) TYPE: amino acid
        (D) TOPOLOGY: linear (ii) MOLECULE TYPE:
        (A) DESCRIPTION: protein (iii) HYPOTHETICAL:Yes (vi) ORIGINAL SOURCE:
        (A) ORGANISM: Yarrowia lypolytica (xi) SEQUENCE DESCRIPTION: SEQ ID NO:32:

```
Met Thr Ala Pro Val Lys Leu His Leu Arg Ala Glu Thr Lys Pro
1               5                   10                  15

Leu Glu His Arg Ser Ala Leu Thr Pro Thr Thr Thr Arg Lys Leu
                20                  25                  30

Leu Asp Ala Gly Phe Glu Val Phe Val Glu Lys Ser Pro Leu Arg
            35                  40                  45

Ile Phe Asp Asp Gln Glu Phe Val Asp Val Gly Ala Thr Leu Val
        50                  55                  60

Val Glu Glu Gly Ser Trp Val Ser Ala Pro Glu Asp Arg Met Ile
    65                  70                  75

Ile Gly Leu Lys Glu Leu Pro Glu Glu Ser Phe Pro Leu Ser His
80                  85                  90

Glu His Ile Gln Phe Ala His Cys Tyr Lys Asp Gln Gly Gly Trp
            95                  100                 105

Lys Asp Val Leu Ser Arg Phe Pro Ala Gly Asn Gly Thr Leu Tyr
        110                 115                 120

Asp Leu Glu Phe Leu Glu Asp Asp Asn Gly Arg Arg Val Ala Ala
    125                 130                 135

Phe Glu Phe His Ala Gly Phe Ala Gly Ala Ala Ile Gly Val Glu
150                 145                 150

Thr Trp Ala Phe Gln Gln Thr His Pro Asp Ser Glu Asn Leu Pro
            155                 160                 165
```

Gly Val Ser Ala Tyr Pro Asn Glu Thr Glu Leu Val Asp Lys Ile
                170                 175                 180

Lys Lys Asp Leu Ala Ala Ala Val Glu Lys Gly Ser Lys Leu Pro
                185                 190                 195

Thr Val Leu Val Ile Gly Ala Leu Gly Arg Cys Gly Ser Gly Ala
                200                 205                 210

Ile Asp Leu Ala Arg Lys Val Gly Ile Pro Glu Glu Asn Ile Ile
                215                 220                 225

Arg Trp Asp Met Asn Glu Thr Lys Lys Gly Gly Pro Phe Asp Glu
                230                 235                 240

Ile Ala Asp Ala Asp Ile Phe Ile Asn Cys Ile Tyr Leu Ser Gln
                245                 250                 255

Pro Ile Pro Pro Phe Ile Asn Tyr Asp Leu Leu Asn Lys Glu Thr
                260                 265                 270

Arg Lys Leu Ser Val Ile Val Asp Val Ser Ala Asp Thr Thr Asn
                275                 280                 285

Pro His Asn Pro Val Pro Val Tyr Thr Ile Ala Thr Thr Phe Asp
                290                 295                 300

His Pro Thr Val Pro Val Glu Thr Thr Ala Gly Pro Lys Leu Ser
                305                 310                 315

Val Cys Ser Ile Asp His Leu Pro Ser Leu Leu Pro Arg Glu Ala
                320                 325                 330

Ser Glu Ala Phe Ser Glu Ala Leu Leu Pro Ser Leu Leu Gln Leu
                335                 340                 345

Pro Gln Arg Asp Thr Ala Pro Val Trp Thr Arg Ala Lys Ala Leu
                350                 355                 360

Phe Asp Lys His Val Leu Arg Ile Gly Glu
                365                 370

(2) INFORMATION FOR SEQ ID NO:33:

(i) SEQUENCE CHARACTERISTICS:
        (A) LENGTH: 161 amino acid residues
        (B) TYPE: amino acid
        (D) TOPOLOGY: linear (ii) MOLECULE TYPE:
        (A) DESCRIPTION: peptide (iii) HYPOTHETICAL: Yes (v) FRAGMENT TYPE: internal fragment (vi) ORIGINAL SOURCE:
        (A) ORGANISM: Cryptococcus neoformans (xi) SEQUENCE DESCRIPTION: SEQ ID NO:33:

His Glu His Ile Gln Phe Ala His Cys Tyr Lys Gln Gln Ala Gly
1               5                   10                  15

Trp Asn Asp Val Leu Arg Arg Phe Ala Gln Gly Lys Gly Thr Leu
                20                  25                  30

Tyr Asp Leu Glu Phe Leu Glu Asp Pro Val Ser His Arg Arg Val
                35                  40                  45

Ala Ala Phe Gly Phe His Ala Gly Phe Ala Gly Ala Ala Ala Gly
                50                  55                  60

Ala Leu Ala Phe Ala Ala Gln Gln Thr Gln Asn Gly Gln Gly Lys
                65                  70                  75

Leu Gly Glu Leu Lys Pro Tyr Pro Asn Glu Gly Glu Met Val Lys
                80                  85                  90

```
Glu Val Ser Glu Ala Leu Glu Gly Thr Lys Glu Gly Lys Lys Gly
                95                  100                 105

Val Lys Val Leu Ile Ile Gly Ala Leu Gly Arg Cys Gly Ser Gly
                110                 115                 120

Ala Val Asp Leu Phe Arg Lys Ala Gly Val Ala Glu Glu Asn Ile
                125                 130                 135

Val Lys Trp Asp Met Ala Glu Thr Ala Lys Gly Gly Pro Phe Pro
                140                 145                 150

Glu Ile Leu Asp Val Asp Ile Phe Ile Asn Cys
                155                 160
```